(12) United States Patent
Conklin et al.

(10) Patent No.: US 9,364,322 B2
(45) Date of Patent: Jun. 14, 2016

(54) POST-IMPLANT EXPANDABLE SURGICAL HEART VALVE CONFIGURATIONS

(71) Applicant: Edwards Lifesciences Corporation, Irvine, CA (US)

(72) Inventors: Brian S. Conklin, Orange, CA (US); Louis A. Campbell, Santa Ana, CA (US); Donald E. Bobo, Jr., Santa Ana, CA (US); Steven M. Ford, Laguna Beach, CA (US); Derrick Johnson, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 14/137,501

(22) Filed: Dec. 20, 2013

(65) Prior Publication Data

US 2014/0188219 A1    Jul. 3, 2014

Related U.S. Application Data

(60) Provisional application No. 61/748,022, filed on Dec. 31, 2012.

(51) Int. Cl.
*A61F 2/24* (2006.01)

(52) U.S. Cl.
CPC .............. *A61F 2/2418* (2013.01); *A61F 2/2445* (2013.01); *A61F 2220/0033* (2013.01); *A61F 2220/0075* (2013.01); *A61F 2250/0004* (2013.01); *A61F 2250/0063* (2013.01); *A61F 2250/0071* (2013.01)

(58) Field of Classification Search
CPC .............................. A61F 2/2409; A61F 2/2418
See application file for complete search history.

(56) References Cited

U.S. PATENT DOCUMENTS

| | | |
|---|---|---|
| 3,656,185 A | 4/1972 | Carpentier |
| 4,055,861 A | 11/1977 | Carpentier et al. |
| 4,164,046 A | 8/1979 | Cooley |
| 4,217,665 A | 8/1980 | Bex et al. |
| 4,602,911 A | 7/1986 | Ahmadi et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |

(Continued)

FOREIGN PATENT DOCUMENTS

| | | |
|---|---|---|
| EP | 0338994 A1 | 10/1989 |
| EP | 1034753 A1 | 9/2000 |

(Continued)

*Primary Examiner* — Yashita Sharma
*Assistant Examiner* — Wade P Schutte
(74) *Attorney, Agent, or Firm* — AnneMarie Kaiser; Guy Cumberbatch; Pui Tong Ho

(57) ABSTRACT

Disclosed herein is a prosthetic heart valve, and associated methods therefore, configured to replace a native heart valve, and having a support frame configured to be reshaped into an expanded form in order to receive and/or support an expandable prosthetic heart valve therein. The prosthetic heart valve is configured to have an expansion-resistant configuration when initially implanted to replace a native valve (or other prosthetic heart valve), but to assume a generally expanded form when subjected to an outward force such as that provided by a dilation balloon or other mechanical expander.

20 Claims, 15 Drawing Sheets

(56) References Cited

U.S. PATENT DOCUMENTS

| | | | |
|---|---|---|---|
| 5,306,296 A | 4/1994 | Wright et al. |
| 5,450,860 A | 9/1995 | O'Connor |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,697,382 A | 12/1997 | Love et al. |
| 5,776,189 A | 7/1998 | Khalid |
| 5,824,066 A | 10/1998 | Gross |
| 5,888,240 A | 3/1999 | Carpentier et al. |
| 5,972,030 A | 10/1999 | Garrison et al. |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,348,068 B1 | 2/2002 | Campbell et al. |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,425,916 B1 | 7/2002 | Garrison et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,261,732 B2 | 8/2007 | Justino |
| 7,276,084 B2 | 10/2007 | Yang et al. |
| 7,294,148 B2 | 11/2007 | McCarthy |
| 7,381,218 B2 | 6/2008 | Schreck |
| 7,393,360 B2 | 7/2008 | Spenser et al. |
| 7,399,315 B2 | 7/2008 | Iobbi |
| 7,452,376 B2 | 11/2008 | Lim et al. |
| 7,462,191 B2 | 12/2008 | Spenser et al. |
| 7,470,285 B2 | 12/2008 | Nugent et al. |
| 7,510,575 B2 | 3/2009 | Spenser et al. |
| 7,534,261 B2 | 5/2009 | Friedman |
| 7,556,646 B2 | 7/2009 | Yang et al. |
| 7,585,321 B2 | 9/2009 | Cribier |
| 7,625,403 B2 | 12/2009 | Krivoruchko |
| 7,780,723 B2 | 8/2010 | Taylor |
| 7,806,927 B2 | 10/2010 | Styrc |
| 7,871,436 B2 | 1/2011 | Ryan et al. |
| 8,226,707 B2 | 7/2012 | White |
| 8,236,045 B2 | 8/2012 | Benichou et al. |
| 8,246,677 B2 | 8/2012 | Ryan |
| 8,246,762 B2 | 8/2012 | Janko et al. |
| 8,496,700 B2 | 7/2013 | Edoga et al. |
| 8,500,802 B2 | 8/2013 | Lane et al. |
| 2001/0021874 A1 | 9/2001 | Carpentier et al. |
| 2002/0062150 A1 | 5/2002 | Campbell et al. |
| 2003/0033009 A1 | 2/2003 | Gabbay |
| 2003/0040793 A1 | 2/2003 | Marquez |
| 2003/0199971 A1 | 10/2003 | Tower et al. |
| 2004/0193261 A1 | 9/2004 | Berreklouw |
| 2004/0210305 A1 | 10/2004 | Shu et al. |
| 2004/0249452 A1 | 12/2004 | Adams et al. |
| 2004/0249453 A1 | 12/2004 | Cartledge et al. |
| 2005/0096739 A1 | 5/2005 | Cao |
| 2005/0131533 A1 | 6/2005 | Alfieri et al. |
| 2005/0240200 A1 | 10/2005 | Bergheim |
| 2005/0251251 A1 | 11/2005 | Cribier |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2006/0052867 A1 | 3/2006 | Revuelta et al. |
| 2006/0241748 A1 | 10/2006 | Lee et al. |
| 2007/0016287 A1 | 1/2007 | Cartledge et al. |
| 2007/0067029 A1 | 3/2007 | Gabbay |
| 2007/0100441 A1 | 5/2007 | Kron et al. |
| 2007/0142907 A1 | 6/2007 | Moaddeb et al. |
| 2007/0162111 A1 | 7/2007 | Fukamachi et al. |
| 2007/0244546 A1 | 10/2007 | Francis |
| 2008/0027483 A1 | 1/2008 | Cartledge et al. |
| 2008/0114452 A1 | 5/2008 | Gabbay |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0183285 A1 | 7/2008 | Shaoulian et al. |
| 2008/0200980 A1 | 8/2008 | Robin et al. |
| 2008/0208327 A1 | 8/2008 | Rowe |
| 2008/0208329 A1 | 8/2008 | Bishop et al. |
| 2008/0215144 A1 | 9/2008 | Ryan et al. |
| 2008/0228263 A1 | 9/2008 | Ryan |
| 2008/0243246 A1 | 10/2008 | Ryan et al. |
| 2008/0269878 A1 | 10/2008 | Iobbi |
| 2008/0275549 A1 | 11/2008 | Rowe |
| 2009/0005863 A1 | 1/2009 | Goetz et al. |
| 2009/0082857 A1 | 3/2009 | Lashinski et al. |
| 2009/0093876 A1 | 4/2009 | Nitzan et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192606 A1 | 7/2009 | Gloss et al. |
| 2009/0216322 A1 | 8/2009 | Le et al. |
| 2009/0264989 A1* | 10/2009 | Bonhoeffer et al. ......... 623/1.26 |
| 2009/0281609 A1 | 11/2009 | Benichou et al. |
| 2010/0076548 A1 | 3/2010 | Konno |
| 2010/0076549 A1 | 3/2010 | Keidar et al. |
| 2011/0166636 A1 | 7/2011 | Rowe |
| 2011/0178597 A9 | 7/2011 | Navia et al. |
| 2011/0224781 A1 | 9/2011 | White |
| 2011/0230956 A1 | 9/2011 | White |
| 2011/0245918 A1 | 10/2011 | White |
| 2011/0264207 A1 | 10/2011 | Bonhoeffer et al. |
| 2011/0288629 A1 | 11/2011 | White |
| 2011/0288632 A1 | 11/2011 | White |
| 2012/0277854 A1 | 11/2012 | Ryan |
| 2012/0283820 A1 | 11/2012 | Tseng et al. |

FOREIGN PATENT DOCUMENTS

| | | | | |
|---|---|---|---|---|
| EP | 1755459 A2 | 2/2007 | | |
| EP | 1804726 A1 | 7/2007 | | |
| EP | 1958598 A1 | 8/2008 | | |
| WO | 2004006810 A1 | 1/2004 | | |
| WO | 2012018779 A2 | 2/2012 | | |
| WO | WO 2012/018779 | * | 2/2012 | ................ A61F 2/24 |

* cited by examiner

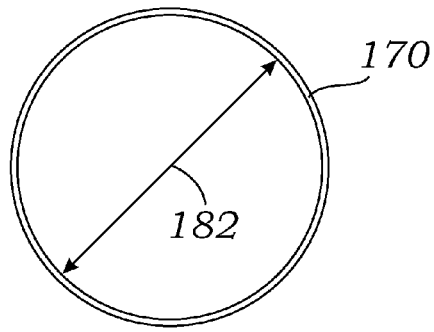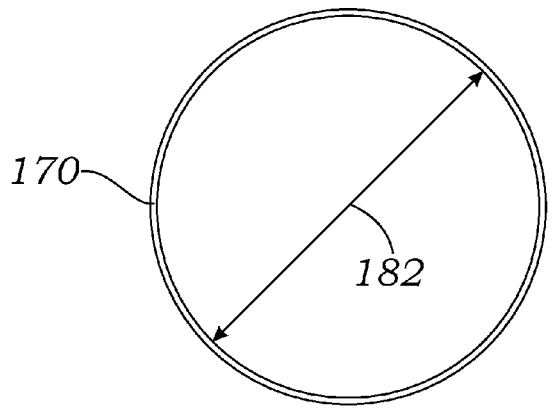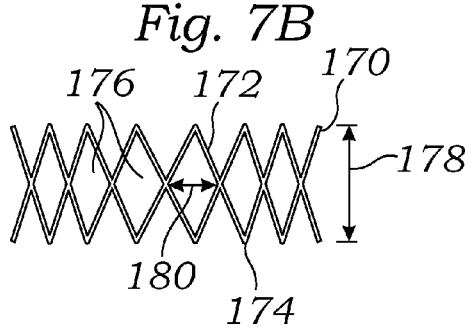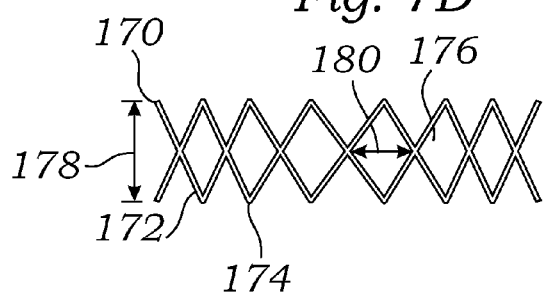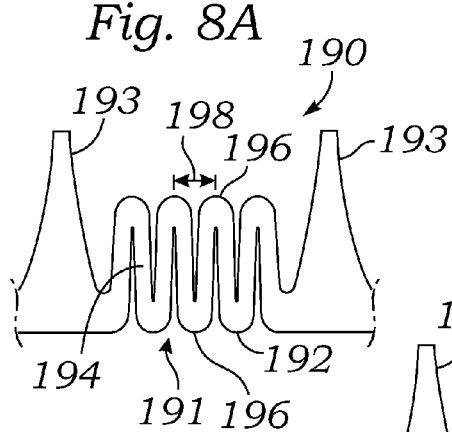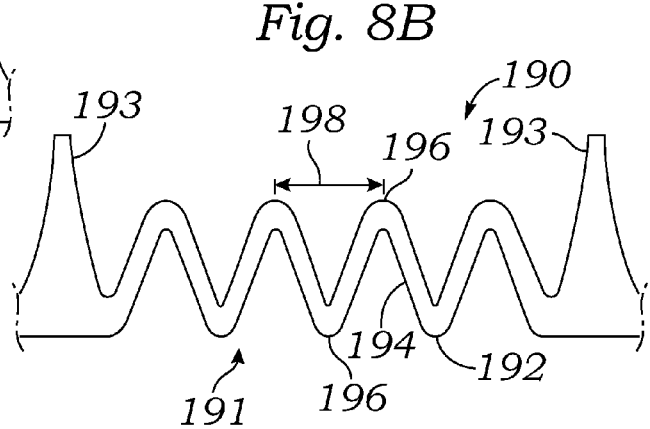

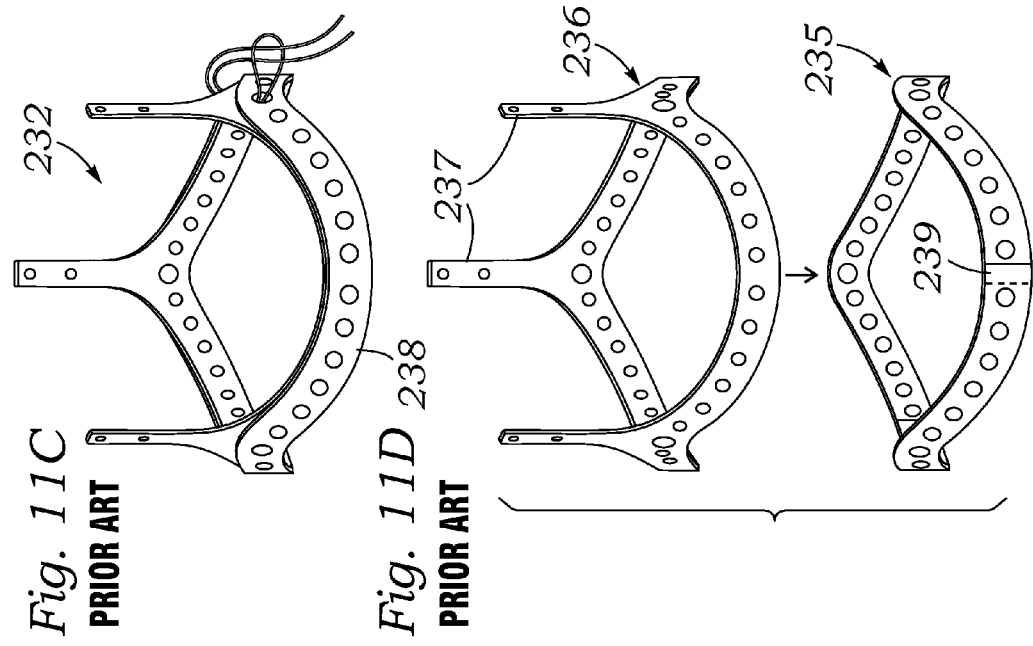
*Fig. 11C* PRIOR ART
*Fig. 11D* PRIOR ART
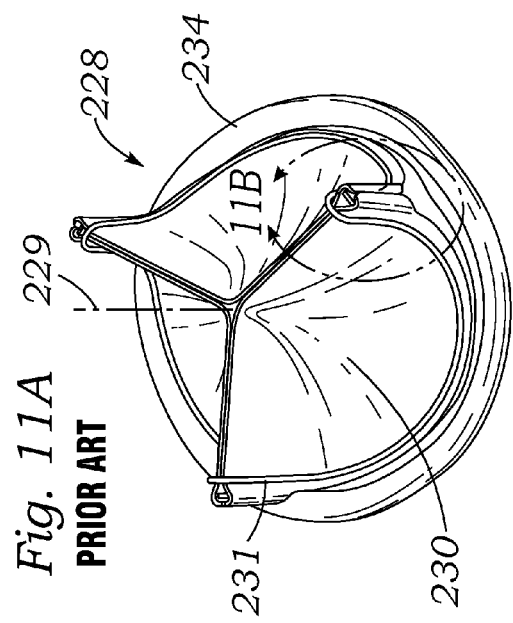
*Fig. 11A* PRIOR ART
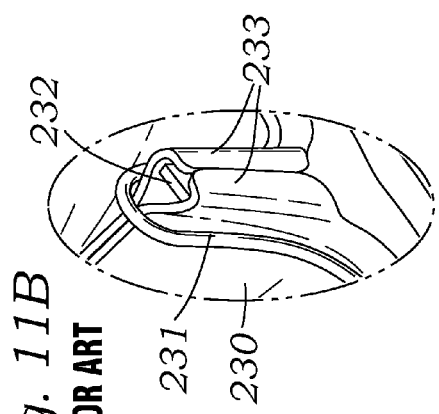
*Fig. 11B* PRIOR ART

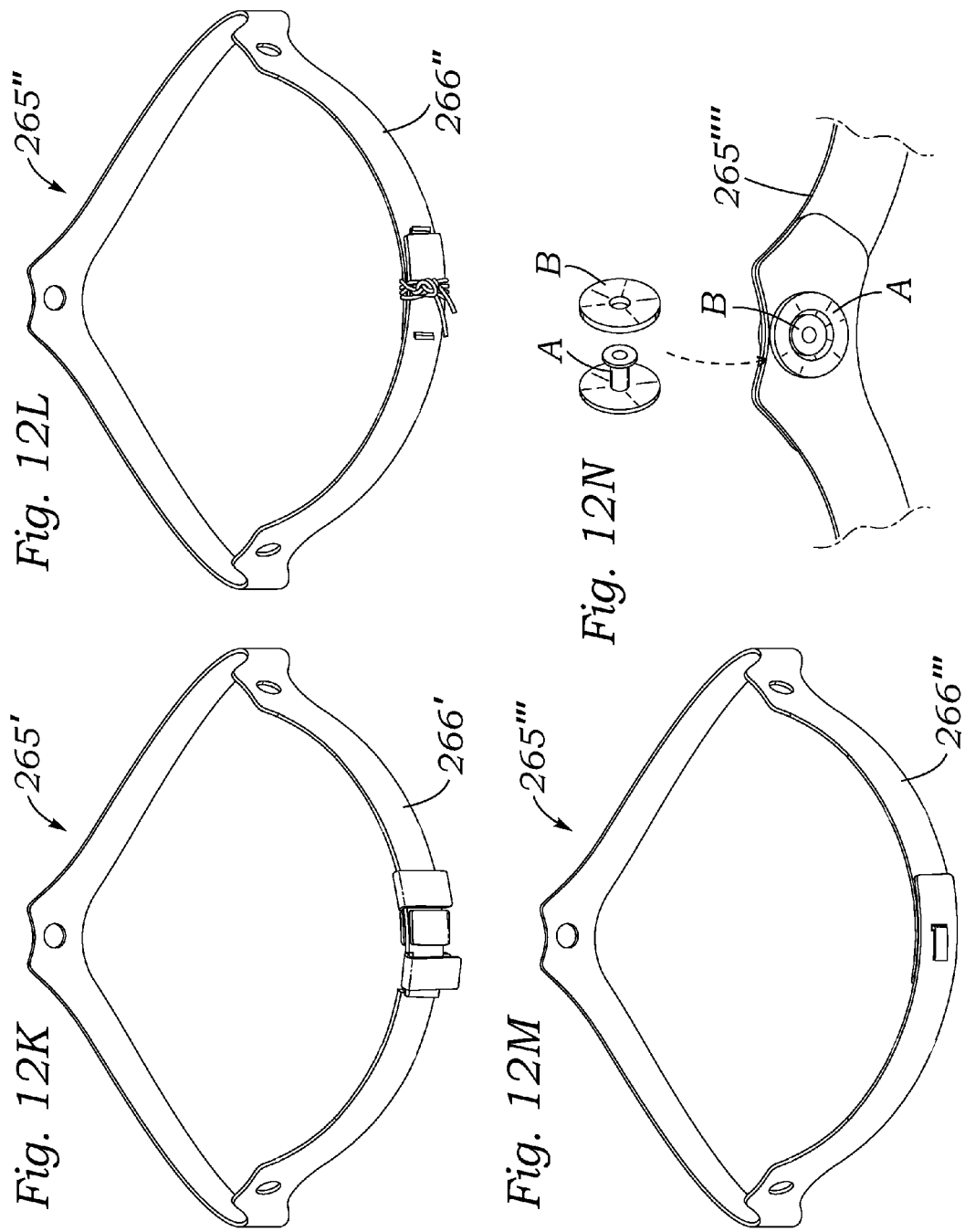

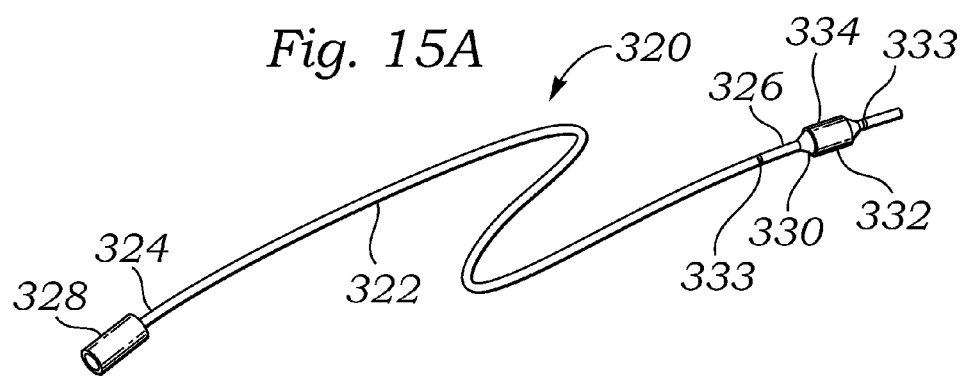
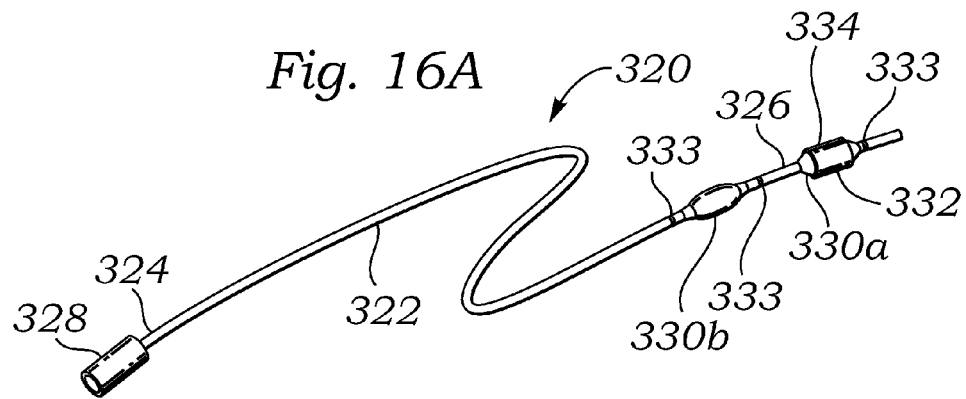

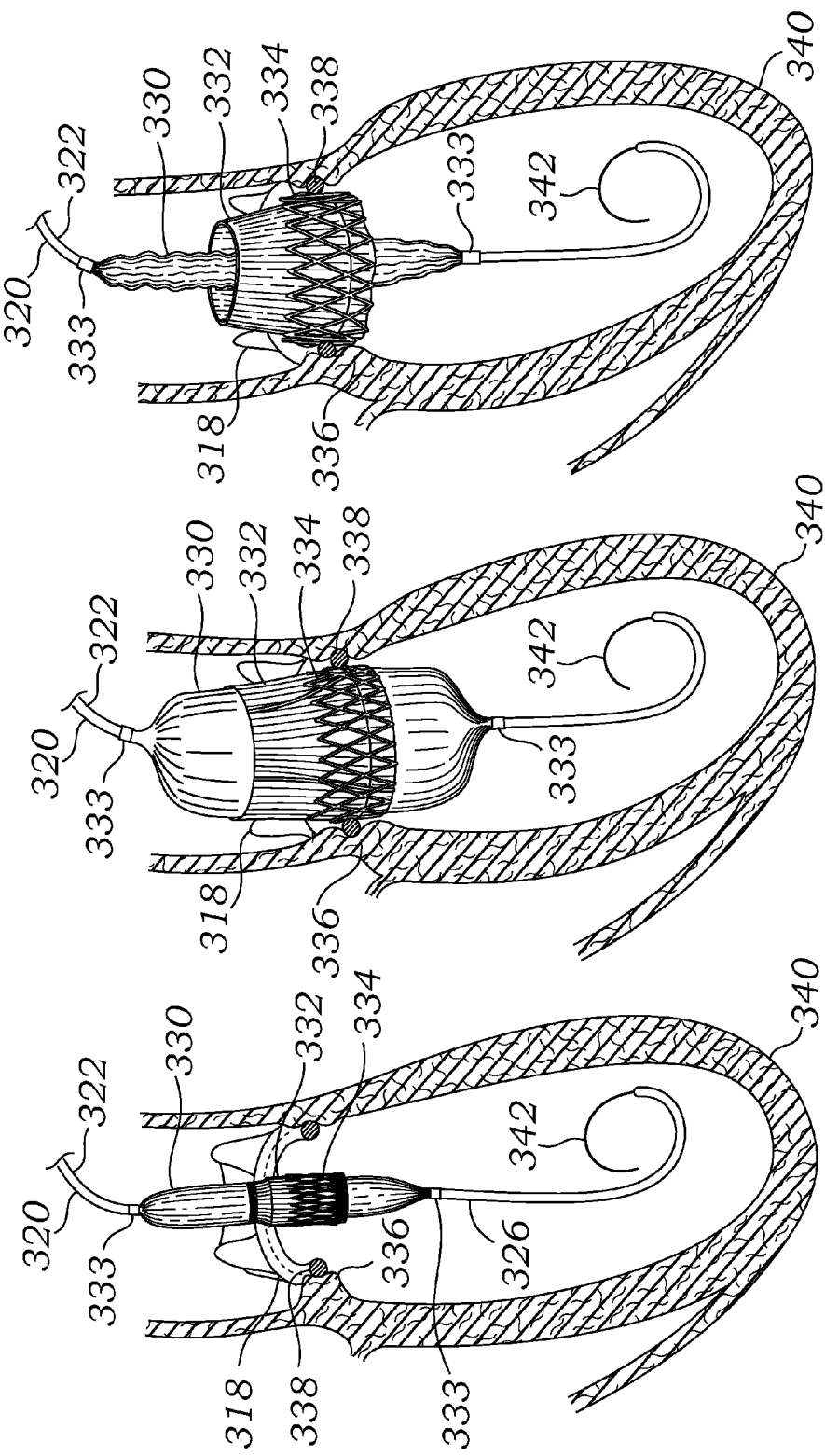

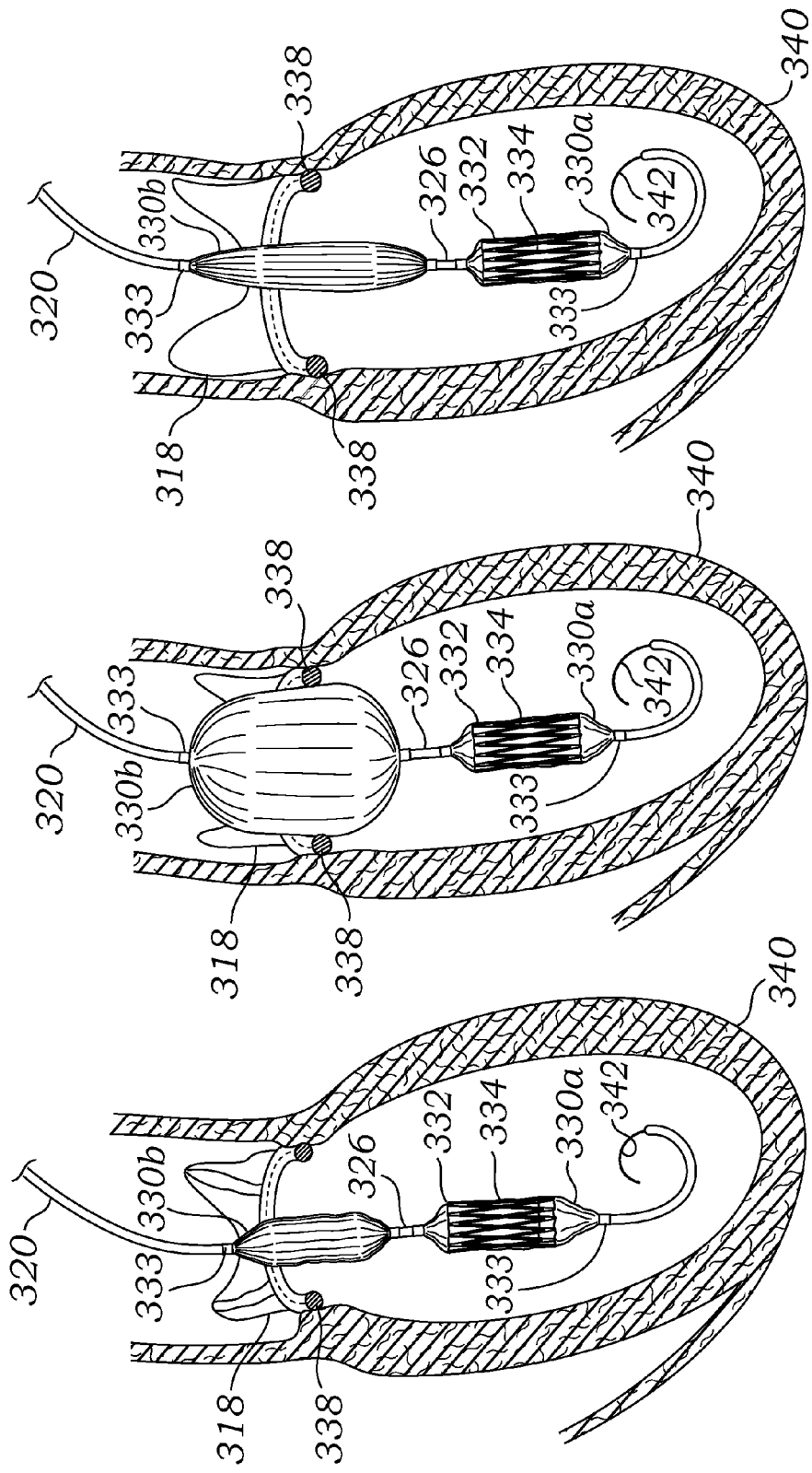

POST-IMPLANT EXPANDABLE SURGICAL HEART VALVE CONFIGURATIONS

RELATED APPLICATIONS

The present application claims priority under 35 U.S.C. §119 to U.S. Provisional Application Ser. No. 61/748,022, filed Dec. 31, 2012. The present application is also related to U.S. patent application Ser. No. 12/234,559, filed Sep. 19, 2008, entitled "Prosthetic Heart Valve Configured to Receive a Percutaneous Prosthetic Heart Valve Implantation," and related to U.S. patent application Ser. No. 12/234,580, filed Sep. 19, 2008, entitled "Annuloplasty Ring Configured to Receive a Percutaneous Prosthetic Heart Valve Implantation," the entire disclosures of which are expressly incorporated herein by reference.

FIELD OF THE INVENTION

The present invention relates to a surgical heart valve for heart valve replacement, and more particularly to a surgical heart valve configured to receive an expandable prosthetic heart valve therein.

BACKGROUND OF THE INVENTION

The heart is a hollow muscular organ having four pumping chambers separated by four heart valves: aortic, mitral (or bicuspid), tricuspid, and pulmonary. Heart valves are comprised of a dense fibrous ring known as the annulus, and leaflets or cusps attached to the annulus.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated. Various surgical techniques may be used to replace or repair a diseased or damaged valve. In a traditional valve replacement operation, the damaged leaflets are typically excised and the annulus sculpted to receive a replacement prosthetic valve.

A prosthetic heart valve typically comprises a support structure (such as a ring and/or stent) with a valve assembly deployed therein. The support structure is often rigid, and can be formed of various biocompatible materials, including metals, plastics, ceramics, etc. Two primary types of "conventional" heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the entire disclosures of which are hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabric (e.g., Dacron) coverings, and a fabric-covered sewing ring is provided on the inflow end of the peripheral support structure.

One example of the construction of a flexible leaflet valve is seen in U.S. Pat. No. 6,585,766 to Huynh, et al. (issued Jul. 1, 2003), in which the exploded view of FIG. 1 illustrates a fabric-covered wireform 54 and a fabric-covered support stent 56 on either side of a leaflet subassembly 52. The contents of U.S. Pat. No. 6,585,766 are hereby incorporated by reference in their entirety. Other examples of valve and related assemblies/systems are found in U.S. Pat. No. 4,084,268, which issued Apr. 18, 1978; U.S. Pat. No. 7,137,184, which issued on Nov. 21, 2006; U.S. Pat. No. 8,308,798, filed Dec. 10, 2009; U.S. Pat. No. 8,348,998, filed Jun. 23, 2010; and U.S. Patent Publication No. 2012/0065729, filed Jun. 23, 2011; the entire contents of each of which are hereby incorporated by reference in their entirety.

Sometimes the need for complete valve replacement may arise after a patient has already had an earlier valve replacement for the same valve. For example, a prosthetic heart that was successfully implanted to replace a native valve may itself suffer damage and/or wear and tear many years after initially being implanted. Implanting the prosthetic heart valve directly within a previously-implanted prosthetic heart valve may be impractical, in part because the new prosthetic heart valve (including the support structure and valve assembly) will have to reside within the annulus of the previously-implanted heart valve, and traditional prosthetic heart valves may not be configured to easily receive such a valve-within-a-valve implantation in a manner which provides secure seating for the new valve while also having a large enough annulus within the new valve to support proper blood flow therethrough.

Some attention has been paid to the problem of implanting a new valve within an old valve. In particular, the following disclose various solutions for valve-in-valve systems: U.S. Patent Publication No. 2010/0076548, filed Sep. 19, 2008; and U.S. Patent Publication No. 2011/0264207, filed Jul. 7, 2011.

Despite certain advances in the valve-in-valve area, there remains a need for a prosthetic heart valve which can properly replace a damaged heart valve, such as a prosthetic valve configured to replace a native valve via surgical implantation, but which also enable a replacement expandable prosthetic heart valve to be deployed therein at a later time without loss of flow capacity. The current invention meets this need.

SUMMARY OF THE INVENTION

The present application discloses a number of prosthetic heart valves each having an inflow end and an outflow end. The prosthetic heart valves have a first unexpanded configuration and a second expanded configuration, and include a support structure that resists compression of the valve smaller than the unexpanded configuration, and enables expansion to the expanded configuration. Desirably, the heart valves prevent compression when subjected to a compressive force of between 1 and 5 atmospheres, and circumferentially expand from a first diameter to a second diameter when subjected to a dilation force of between 1 to 12 atmospheres, though between 1 and 8 atmospheres is more likely.

In one embodiment, the support structure defines a valve orifice and comprises multiple commissural supports or posts projecting in an outflow direction. A valve portion supported by the support structure comprises multiple leaflets, wherein adjacent leaflets are secured at their edges to the commissural supports. When the prosthetic heart valve is in the first unexpanded configuration, each leaflet is configured to coapt with adjacent leaflets to permit blood to flow through the prosthetic heart valve from an inflow end to the outflow end, but to prevent blood from flowing through the prosthetic heart valve from the outflow end to the inflow end.

The present application discloses a prosthetic heart valve having an inflow end and an outflow end, and the valve has a first unexpanded configuration and a second expanded configuration. The valve includes an inner support structure defined around a valve orifice. The support structure has a first inner diameter when the prosthetic heart valve is in the first unexpanded configuration and a second inner diameter when the prosthetic heart valve is in the second expanded configuration, and is configured when in the first unexpanded configuration to resist inward compression of the support structure and to permit radial expansion thereof to the second inner diameter when subjected to a dilation force, but prevents radial expansion thereof to a diameter larger than the second inner diameter when subjected to the dilation force. The support structure comprises a support ring including at least one expansion segment that will plastically expand when subjected to the dilation force, and the valve has a valve portion supported by the support structure that allows for one-way blood flow through the valve when the valve is in the first unexpanded configuration.

The expansion segment may comprise a series of interconnected struts connected end-to-end by hinge-like connections which form a zig-zag accordion-like structure having substantially diamond-shaped cells. In one form, the support ring has an undulating shape with alternating cusps and commissures, and wherein the support ring comprises a plurality of expansion segments located between commissures. The expansion segments may be a substantially serpentine structure formed by metallic struts, wherein the struts are compressed closely together, with minimal distances between adjacent struts in the unexpanded configuration to prevent inward compression of the structure to a smaller diameter. The support ring could also be formed of a plurality of segments connected via hinge-like folds which comprise the expansion segments, wherein the ends of adjacent segments initially overlap at the folds such that the support ring has a minimum diameter, and when the support ring expands, the ends of adjacent segments are pulled apart as the folds at least partially unfold, so that the structure has a maximum inner diameter.

Another embodiment disclosed herein is a prosthetic heart valve having a first unexpanded configuration and a second expanded configuration, the prosthetic heart valve comprising a support structure defining a circumference. The support structure has a first inner diameter when the prosthetic heart valve is in the first unexpanded configuration and a second inner diameter when the prosthetic heart valve is in the second expanded configuration, wherein the second inner diameter is larger than the first inner diameter. The support structure rigidly resists inward compression when the prosthetic heart valve is in the first unexpanded configuration. The support structure comprises a first support band passing substantially around the circumference of the support structure. The first support band can comprise a polymeric material. A second support band passes substantially around the circumference of the support structure and is arranged concentrically against the first support band. The second support band can comprise a metal, and the second support band has at least one expansion point around its circumference configured to permit expansion of the second support band when the support structure is subjected to a dilation force significantly greater than forces associated with normal cardiac cycling. The first support band and the second support band are secured together at at least one point around the circumference of the support structure, and the valve has a valve portion supported by the support structure allows for one-way blood flow through the valve when the valve is in the first unexpanded configuration.

The first support band desirably has a first weakened section configured to stretch or structurally fail when the support structure is subjected to the dilation force. The second support band further may have a second weakened section at the location of the first weakened section configured to structurally fail when the support structure is subjected to the dilation force. In one embodiment, the second inner diameter is fixed so that the support structure will not expand past the second inner diameter when subjected to the dilation force.

The at least one expansion point in the second support band includes overlapping free ends with at least one hole each that register and a suture passed through the registered holes that maintains the free ends aligned but is configured to break when the support structure is subjected to the dilation force. Preferably, the second support band has an undulating shape with alternating cusps and commissures, and the free ends overlap at either one of the cusps or one of the commissures. The free ends may include interlaced tabs that engage one another to maintain alignment of the free ends, or the free ends overlap with one outside the other and a sleeve surrounds them to maintain alignment of the free ends. In another embodiment, one free end comprises a pin that resides in a slot in the other free end, wherein the pin is configured to slide within the slot. Further, the support ring may comprise three segments having mutually overlapping free ends.

In one embodiment, the support structure comprises a support ring formed of an inner ring and an outer ring, wherein the inner ring has a substantially continuous structure around the periphery of the support ring, and the outer ring has a segmented structure formed by a plurality of discrete segments in sliding contact with an outer face of the inner ring. The inner ring resists outward expansion from an outward force such as from a balloon catheter to a much greater extent than the segments of the outer ring, and the support ring prevents compression of the support structure when the prosthetic heart valve is in the unexpanded configuration. Preferably, there are the same number of discrete segments in the outer ring as the number of commissure supports, with each discrete segment being located between adjacent commissural supports. The inner ring of the support ring may be formed of an elastic material that will stretch upon being subjected to the dilation force. The discrete segments of the outer ring may be separated by breaks or weakened portions.

In a further configuration, the support structure is substantially circular and comprises a support ring having a plurality of arcuate segments extending around the circumference thereof. Ends of adjacent arcuate segments overlap and are secured to each other at connections to form a weaken portion that will structurally fail when subjected to the dilation force. The connections may be spot welds, sonic welds, and/or adhesive. Further, each arcuate segment has opposite ends, wherein each connection may comprises a pin in an end of one arcuate segment residing in a slot in an adjacent segment, and wherein the pin is configured to slide within the slot. The pins may have an enlarged distal portion having a diameter larger than the slot width, which thereby prevents the pin from being pulled out of the slot. Each pin desirably has a substantially round or a substantially elongated cross section. Each pin may reside very tightly within the slot, so that the pin will not slide within the slot unless the valve is subjected to the dilation force. In one version, each pin is fixedly held at a specific position within the slot such as via adhesive or spot-welding that is configured to fail and permit the pin to slide when the valve is subjected to the dilation force. There are desirably at least three overlapping segments, and potentially up to six.

A still further heart valve support structure comprises a support ring including a plurality of weakened portions that will plastically expand when subjected to the dilation force. For instance, the support ring may comprise a series of interconnected struts connected end-to-end by hinge-like connections which form the weakened portions to form a zig-zag accordion-like structure having substantially diamond-shaped cells. In one embodiment, the support ring comprises a plurality of expansion segments located between commissural supports. The expansion segments may comprise a substantially serpentine structure formed by metallic struts. Preferably, the struts are compressed closely together, with minimal distances between adjacent struts in the unexpanded configuration to prevent inward compression of the structure to a smaller diameter. Alternatively, the support ring is formed of a plurality of segments connected via hinge-like folds which form the weakened portions, wherein the ends of adjacent segments initially overlap at the folds such that the support ring has a minimum diameter, and when the support ring expands, the ends of adjacent segments are pulled apart as the folds at least partially unfold, so that the structure has a maximum inner diameter.

In yet another embodiment, the prosthetic heart valve comprises a support structure defining a circumference, the support structure having a first inner diameter when the prosthetic heart valve is in the first unexpanded configuration and a second inner diameter when the prosthetic heart valve is in the second expanded configuration. The second inner diameter is larger than the first inner diameter. The support structure resists inward compression when the prosthetic heart valve is in the first unexpanded configuration. The support structure comprising a support band with overlapping free ends with at least one hole each that register and a weakened section comprising a suture passing through the registered holes that maintains the free ends aligned but is configured to structurally fail when the support structure is subjected to a dilation force greater than forces associated with normal cardiac cycling. The valve also includes a valve portion supported by the support structure that allows for one-way blood flow through the valve when the valve is in the first unexpanded configuration. The support band can comprise a metal, and have an undulating shape with alternating cusp and commissure portions, and the free ends can overlap at one of the cusp portions or at one of the commissure portions. The support structure can also include a second support portion comprising a polymeric material passing substantially around the circumference of the support structure and arranged concentrically within the support band. The support band and the second support portion are preferably secured together at at least one point around the circumference of the support structure. The second support portion can include a second weakened section configured to stretch or structurally fail when the support structure is subjected to the dilation force.

The prosthetic heart valve described herein is configured to receive a prosthetic heart valve, such as a catheter-deployed (transcatheter) prosthetic heart valve, therein. In one embodiment, the prosthetic heart valve has a support structure which is substantially resistant to radial compression (and which may be substantially resistant to radial expansion) when deployed in the patient's native heart valve annulus to replace the native heart valve (or to replace another prosthetic heart valve), but is configured to be radially expandable, and/or to transform to a generally expanded and/or expandable configuration, in order to receive a prosthetic heart valve therein, such as a percutaneously-delivered prosthetic heart valve. The transformation from expansion-resistant to expanded/expandable can be achieved by subjecting the expansion-resistant support structure to an outward force, such as a dilation force, which may be provided by a dilation balloon used to deploy a replacement prosthetic valve.

The prosthetic heart valve structure may be generally rigid prior to dilation, and may be configured to become generally non-rigid, and even generally elastic, when subjected to an outward force. The elasticity may assist in holding a percutaneously-introduced prosthetic valve within the current prosthetic valve structure. The prosthetic heart valve structure may be configured to be resistant to radial compression, but to permit radial expansion when subjected to radially expansive forces, and potentially to even relatively small radially expansive forces.

The prosthetic valve can be initially deployed in the patient's valve annulus using various surgical techniques (e.g., traditional open-chest, minimally-invasive, percutaneous, etc.) to correct heart valve function. If the heart valve function declines further after deployment of the prosthetic valve, a new replacement prosthetic valve can be deployed within the previously-deployed prosthetic valve without the need to excise the previously-deployed prosthetic valve. Deployment of the replacement prosthetic valve within the previously-deployed prosthetic valve can occur at a much later time from initial deployment of the previously-deployed prosthetic valve. The prosthetic valve disclosed herein is thus configured to be deployed in a patient and, at a later time, to accept and even improve deployment of a replacement prosthetic valve within the same valve annulus.

A method for repairing a patient's heart function according to an embodiment of the invention can include: providing a prosthetic heart valve configured to have a generally rigid and/or expansion-resistant support structure upon implantation and also configured to assume a expanded/expandable configuration upon dilation; and implanting the prosthetic heart valve in a heart valve annulus. The method may also include deploying an expandable prosthetic heart valve within the previously-deployed heart valve and heart valve annulus. Deploying the expandable prosthetic heart valve within the previously-deployed prosthetic valve and heart valve annulus may include dilating the previously-deployed prosthetic valve to cause the previously-deployed prosthetic valve to assume a generally expanded/expandable shape.

Dilating a previously-deployed prosthetic heart valve may include using a dilation balloon, such as the type currently used for dilation of native heart valves, which can be advanced within the previously-deployed prosthetic heart valve and expanded to a desired pressure and/or diameter. As a general rule, dilation balloons used for dilation of native valves are formed from generally inelastic material to provide a generally fixed (i.e., pre-set) outer diameter when inflated.

Once such balloons are inflated to their full fixed diameter, they will not appreciably expand further (prior to rupturing) even if additional volume/pressure is added therein. Typical pressures for inflating such balloons are between 1 and 12, and more preferably between 1 and 8 atmospheres, with pre-set inflated outer diameters of such balloons being on the order of 18 to 33 millimeters. The dilation balloon may be expanded to a desired pressure (e.g., 1-12 atmospheres) sufficient to fully inflate the dilation balloon to its desired diameter and to dilate and expand the previously-deployed prosthetic heart valve.

In one embodiment, the dilation balloon is configured with a pre-set inflated outer diameter which is larger, such as by 2 to 3 mm, or 10-20% or more, than the inner diameter of the previously-deployed prosthetic heart valve. As an example, if the previously-deployed prosthetic heart valve of the invention has an inner diameter of 23 mm, a dilation balloon having an inflated diameter of 24-27 mm may be inflated within the prosthetic heart valve to cause it to expand and/or become elastic.

In the expanded configuration, the leaflets of the prosthetic heart valve (which had coapted to control blood flow prior to expansion) may not coapt as well, or not at all. Accordingly, the leaflets (post-expansion) may permit substantial blood to flow in both directions. The leaflets are thus largely ineffective in controlling blood flow post-expansion. Control of the blood flow will thus be assumed by a newly implanted prosthetic valve deployed within the orifice of the prior (and now-dilated) prosthetic valve.

Non-limiting examples of inner diameters/orifices (pre- and post-expansion) of embodiments of the current invention include: 15 mm which expands to 17 or 18 mm; 17 mm which expands to 19 or 20 mm; 19 mm which expands to 21 or 22 mm; 22 mm which expands to 24 or 25 mm; 25 mm that expands to 28 mm; 27 mm that expands to 30 mm; 30 mm which expands to 33 mm.

Prosthetic heart valves according to various embodiments of the invention can be configured to be generally rigid prior to dilation, but become expanded and/or elastic when subjected to a sufficient dilation pressure. For example, a prosthetic heart valve could be configured to withstand naturally occurring dilation pressures that may occur during beating of the heart, but to become expanded and/or elastic when subjected to a desired pressure (e.g., from a dilation balloon or other mechanical expander), such as a pressure of 1 atmosphere, 2 atmospheres, 3 atmospheres, 4 atmospheres, 5 atmospheres, or 6 atmospheres, depending on the particular application.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 7A-7B depict top and side views, respectively, of a prosthetic heart valve, pre-dilation, according to an embodiment of the invention;

FIGS. 7C-7D depict top and side views, respectively, of the support structure of FIGS. 7A-7B after the prosthetic heart valve support structure has been dilated;

FIGS. 8A-8B depict side views, pre-dilation and post-dilation, respectively, of a prosthetic heart valve support structure according to an embodiment of the invention;

FIGS. 11A-11D are perspective and exploded views of an exemplary prosthetic heart valve of the prior art having inner structural bands;

FIGS. 12K-12N show further variations on the first prosthetic heart valve support band;

FIG. 15A depicts an expandable prosthetic heart valve deployment catheter configured for prosthetic heart valve deployment according to an embodiment of the invention;

FIG. 15B depicts the expandable prosthetic heart valve deployment catheter of FIG. 15A positioned within a previously-deployed prosthetic heart valve in a heart valve annulus of a patient according to an embodiment of the invention;

FIG. 15C depicts the expandable prosthetic heart valve deployment catheter of FIG. 15A dilating the previously-deployed prosthetic heart valve and deploying an expandable prosthetic heart valve therewithin according to an embodiment of the invention;

FIG. 15D depicts the expandable prosthetic heart valve deployment catheter of FIG. 15A being withdrawn from the patient according to an embodiment of the invention;

FIG. 16A depicts an expandable prosthetic heart valve deployment catheter configured for dilation of a previously-deployed prosthetic heart valve and for deployment of an expandable prosthetic heart valve according to an embodiment of the invention;

FIG. 16B depicts the expandable prosthetic heart valve deployment catheter of FIG. 16A with the dilation balloon positioned within the previously-deployed prosthetic heart valve in the heart valve annulus according to an embodiment of the invention;

FIG. 16C depicts the expandable prosthetic heart valve deployment catheter of FIG. 16A dilating the previously-deployed prosthetic heart valve according to an embodiment of the invention; and FIG. 16D depicts the expandable prosthetic heart valve deployment catheter of FIG. 16A with the dilation balloon deflated after dilation of the previously-deployed prosthetic heart valve according to an embodiment of the invention.

DETAILED DESCRIPTION OF THE PREFERRED EMBODIMENTS

Figure 1:
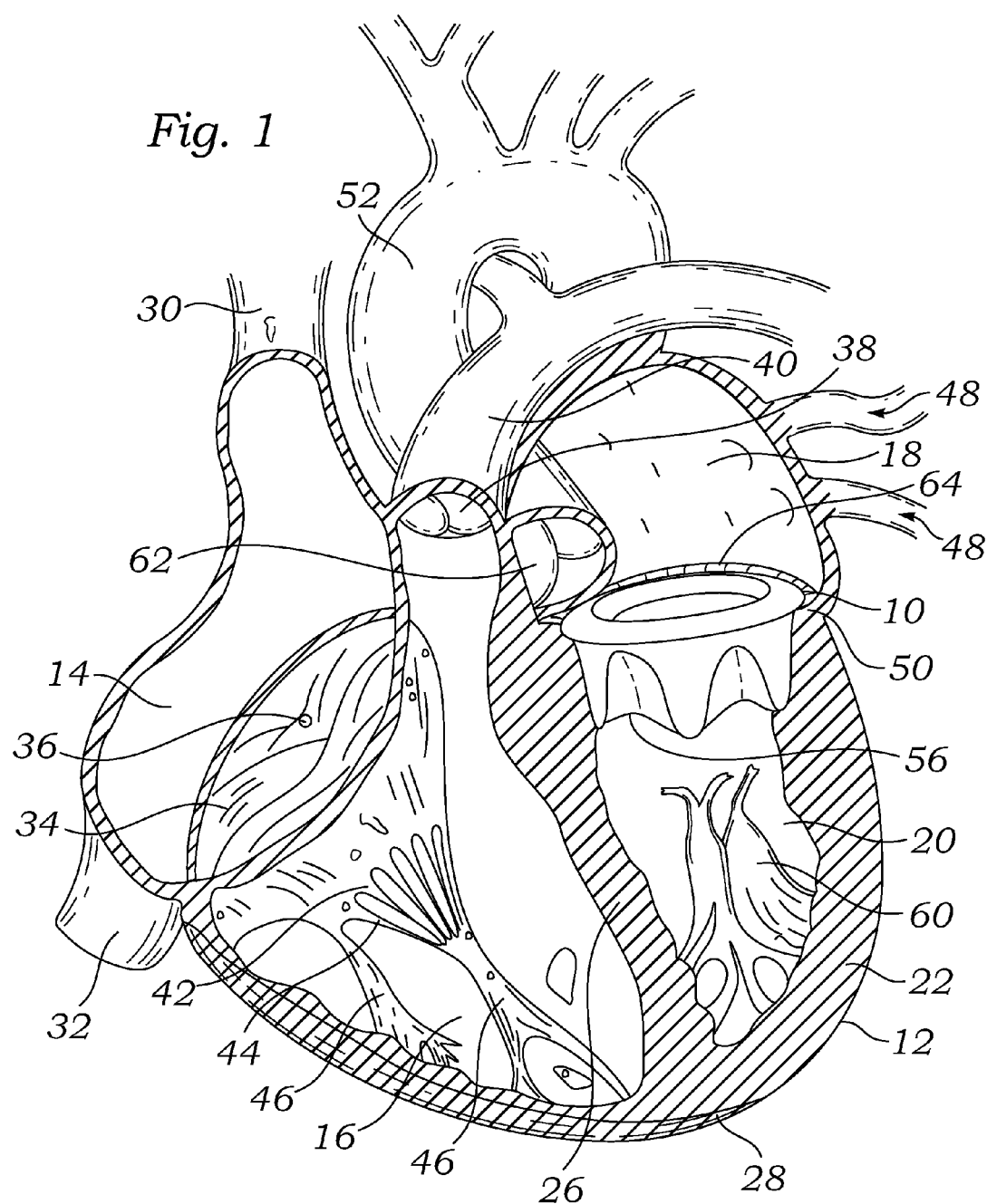
FIG. 1 depicts a prosthetic heart valve deployed in a heart according to an embodiment of the invention.

With reference to FIG. 1, a prosthetic heart valve 10 according to the invention is depicted in a heart 12. The heart 12 has four chambers, known as the right atrium 14, right ventricle 16, left atrium 18, and left ventricle 20. The general anatomy of the heart 12, which is depicted as viewed from the front of a patient, will be described for background purposes. The heart 12 has a muscular outer wall 22, with an interatrial septum 24 dividing the right atrium 14 and left atrium 18, and a muscular interventricular septum 26 dividing the right ventricle 16 and left ventricle 20. At the bottom end of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 through the pulmonary valve 38 to the pulmonary artery 40 which branches into arteries leading to the lungs (not shown). Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendinae 44 to papillary muscles 46 in the right ventricle 16 for controlling the movements of the tricuspid valve 34.

After exiting the lungs, the newly-oxygenated blood flows through the pulmonary veins 48 and enters the left atrium 18 of the heart 12. The mitral valve in a normal heart controls blood flow between the left atrium 18 and the left ventricle 20. Note that in the current figure, the native mitral valve has been replaced with the prosthetic heart valve 10, which is accordingly a prosthetic mitral valve 50. The prosthetic mitral valve 50 is closed during ventricular systole when blood is ejected from the left ventricle 20 into the aorta 52. Thereafter, the prosthetic mitral valve 50 is opened to refill the left ventricle 20 with blood from the left atrium 18. Blood from the left ventricle 20 is pumped by power created from the musculature of the heart wall 22 and the muscular interventricular septum 26 through the aortic valve 62 into the aorta 52 which branches into arteries leading to all parts of the body.

In the particular embodiment depicted, the prosthetic heart valve 10 is deployed to replace a native mitral valve, and more particularly is secured (via, e.g., sutures) adjacent and around the mitral valve annulus 64. Depending on the particular application, including the method by which the prosthetic heart valve 10 was implanted, the particular native valve (aortic, mitral, tricuspid, etc.) and/or some or all of its associated structures may be entirely or partially removed prior to or during implantation of the prosthetic heart valve 10, or the native valve and/or some or all associated structures may simply be left in place with the prosthetic heart valve 10 installed over the native valve. For example, a native mitral valve typically has two leaflets (anterior leaflet and posterior leaflet), lower portions and free edges of which are connected via mitral chordae tendinae to papillary muscles 60 in the left ventricle 20 for controlling the movements of the mitral valve. Not all of these structures (i.e., mitral valve leaflets, chordae tendinae) are depicted in FIG. 1 because, in the particular embodiment, the native mitral valve and many associated structures (chordae, etc.) have been removed prior to or during implantation of the prosthetic heart valve 10. However, in many prosthetic valve implantations, surgeons choose to preserve many of the chordae tendinae, etc., even when excising the native valve.

Although FIG. 1 depicts a prosthetic mitral valve, note that the configurations described herein can be applied to prosthetic valves (and systems and methods therefore) configured to replace any of the heart valves, including aortic, mitral, tricuspid, and pulmonary valves.

Figure 2A:
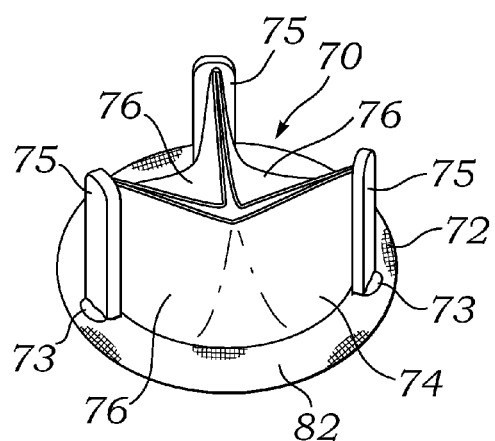
FIGS. 2A-2C depict perspective, top, and side views, respectively, of a prosthetic heart valve according to an embodiment of the invention.
Figure 2B:
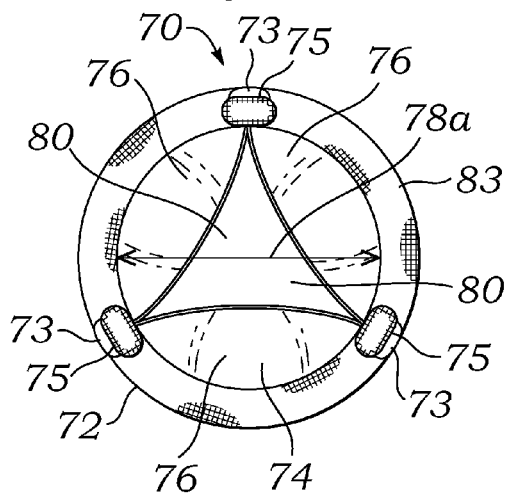
Figure 2C:
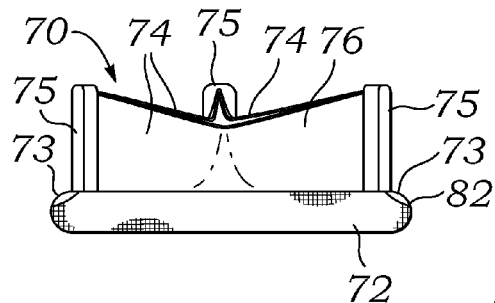

FIGS. 2A-2C depict a prosthetic heart valve 70 according to an embodiment of the invention, where the prosthetic heart valve 70 comprises a support frame 72 and valve structure 74. In the particular embodiment depicted, the valve structure 74 comprises three heart valve leaflets 76. The prosthetic heart valve 70 has an inner diameter 78a of a valve orifice 80 through which blood may flow in one direction, but the valve leaflets 76 will prevent blood flow in the opposite direction. The support frame 72 is generally rigid and/or expansion-resistant in order to maintain the particular shape (which in this embodiment is generally round) and diameter 78a of the valve orifice 80 and also to maintain the respective valve leaflets 76 in proper alignment in order for the valve structure 74 to properly close and open. The particular support frame 72 also includes commissure supports or posts 75 which help support the free edges of the valve leaflets 76. In a preferred construction, each of the valve leaflets 76 attaches along a cusp edge to the surrounding support frame 72 and up along adjacent commissure posts 75. In the particular embodiment depicted in FIGS. 2A-2C, the support frame 72 defines a generally rigid and/or expansion-resistant ring 82 which encircles the valve 70 and defines a generally round valve orifice 80, but other shapes are also within the scope of the invention, depending on the particular application (including issues such as the particular native valve to be replaced, etc.) The particular prosthetic heart valve 70 includes visualization markers 73 (such as radiopaque markers, etc.), which in the current embodiment are on the support frame 72 and correspond to the ring 82 and also to the commissure posts 75 (and hence to the commissures), which can aid in proper placement of a subsequently-deployed expandable prosthetic heart valve within the valve orifice 80 of the prosthetic heart valve 70.

Figure 2D:
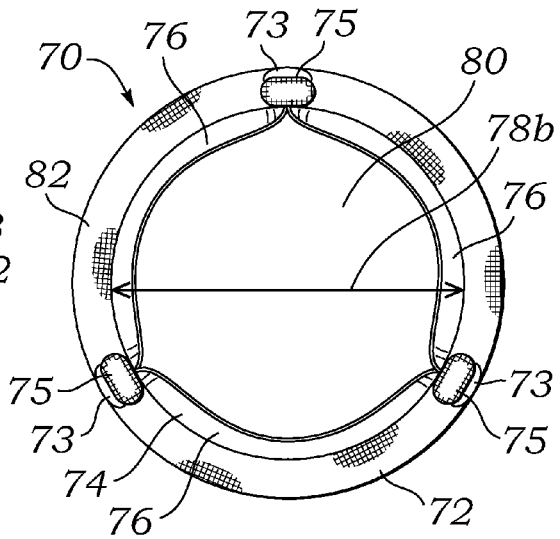
FIG. 2D depicts a top view of the prosthetic heart valve of FIGS. 2A-2C after the prosthetic heart valve has been dilated.

When the prosthetic heart valve 70 of FIGS. 2A-2C is subjected to a dilation force (such as that from a dilation balloon, which may provide pressures of 1 to 12, or more usually 1 and 8, atmospheres), the prosthetic heart valve will be expanded somewhat. The support frame 72 will transition from the generally rigid and/or expansion-resistant configuration of FIGS. 2A-2C to a generally non-rigid and expanded configuration depicted in FIG. 2D. Note that the ring 82, which was generally rigid and/or expansion-resistant, is now expanded, and the valve orifice 80 has accordingly been enlarged to a larger inner diameter 78b. The larger inner diameter 78b is configured to receive an expandable prosthetic heart valve therein. The overall result is that the "post-dilation" prosthetic heart valve 70 of FIG. 2D has a generally larger inner diameter circular opening 78b. The actual inner diameters will depend on the particular application, including aspects of the particular patient's heart (e.g., native valve and/or annulus diameter, etc.). As an example, the pre-dilation inner diameter 78a for a mitral valve may be between 22-30 mm, or for an aortic valve 18-28 mm. The post-dilation inner diameter 78b will be larger, and more specifically large enough to accommodate the outer diameter of an expandable prosthetic valve therein.

In some procedures where an expandable prosthetic heart valve is used to replace/repair a previously-deployed prosthetic heart valve, it may be desirable for the expandable prosthetic heart valve to have a deployed (expanded) inner diameter (and corresponding expandable prosthetic heart valve orifice area) approximately equal to or even greater than the pre-dilation inner diameter 78a (and corresponding pre-dilation prosthetic valve orifice area) of the previously-deployed prosthetic heart valve 70. Such consistency between inner diameters/orifice areas, or improvement thereof, can be useful in maintaining proper blood flow, so that the expandable prosthetic heart valve will provide the same or improved blood flow as was provided by the previously-deployed prosthetic heart valve. Note that the term "valve orifice area" refers to the area of the valve orifice when the valve portion is in the fully open configuration (e.g., with the valve leaflets in their fully open configuration so that the effective orifice area is at its maximum size).

For example, Edwards Lifesciences has Sapien™ expandable prosthetic heart valves having outer diameters of 23 and 26 mm, respectively, which have corresponding inner diameters of about 22 and 25 mm, respectively. Accordingly, the post-dilation inner diameter 78b of the (previously-deployed) prosthetic heart valve may be on the order of 23 and 26 mm (respectively) to accommodate such expandable prosthetic heart valves. This corresponds to a post-dilation inner diameter 78b being about 10 to 20% larger than the pre-dilation inner diameter 78a. Accordingly, embodiments of the invention include a prosthetic heart valve having a post-dilation inner diameter 78b that is about 10, 15, or 20%, or between 5-25%, 10-20%, or 13-17% of the pre-dilation inner diameter 78a.

Note that the invention is not limited to the above differences between pre- and post-dilation inner diameters. For example, there may be applications where much smaller and/or much larger post-dilation inner diameters may be required. In some cases an expandable prosthetic heart valve will have an outer diameter only slightly larger than its inner diameter, so that less expansion of the previously-deployed prosthetic heart valve inner diameter is required in order to accommodate the expandable prosthetic heart valve. In other cases an expandable prosthetic heart valve may have an outer diameter that is much larger than its inner diameter, so that a greater expansion of the previously-deployed prosthetic heart valve inner diameter is necessary to accommodate the expandable prosthetic heart valve. There may also be applications where it may be desirable to deploy an expandable prosthetic heart valve having a smaller or larger inner diameter than was provided by the (previously-deployed and pre-dilation) prosthetic heart valve.

Note that, depending on the particular embodiment, a prosthetic heart valve 70 may return to its pre-dilation inner diameter 78a after being subject to dilation such as from a balloon dilation catheter or other mechanical expander. However, the dilation will have rendered the "post-dilation" prosthetic heart valve 70 into a generally expansion-friendly configuration, so that the "post-dilation" prosthetic heart valve 70 will be forced with relative ease into a larger diameter (such as 78b) when an expandable (e.g., balloon-expandable, self-expanding, etc.) prosthetic heart valve is deployed within the valve orifice 80 of the prosthetic heart valve 70.

The present application discloses a number of different support structures for prosthetic heart valves that can be expanded post-implantation. It should be understood that schematic representations of such support structures are not intended to define the entire support structure, but are depicted for clarity so as to explain better the particular construction. Indeed, a preferred embodiment of a prosthetic heart valve includes the expandable support structure mounted within an overall support structure that includes commissure posts 75 that support flexible valve leaflets 76, such as shown in FIGS. 2A-2D. Alternatively, a prosthetic heart valve including the disclosed expandable support structures may be a mechanical valve with mechanical leaflets. In other words, the overall construction of the prosthetic heart valve should not be considered limited in any claim unless explicitly stated in that claim.

Figure 3A:
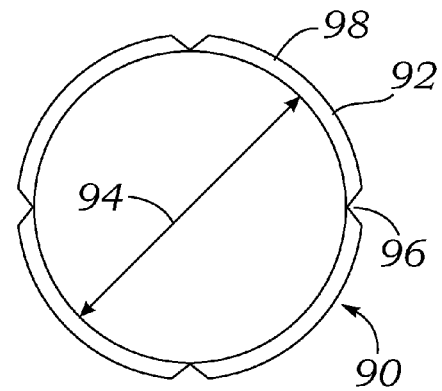
FIGS. 3A-3B depict top views, pre-dilation and post-dilation, respectively, of a prosthetic heart valve support structure according to an embodiment of the invention.
Figure 3B:
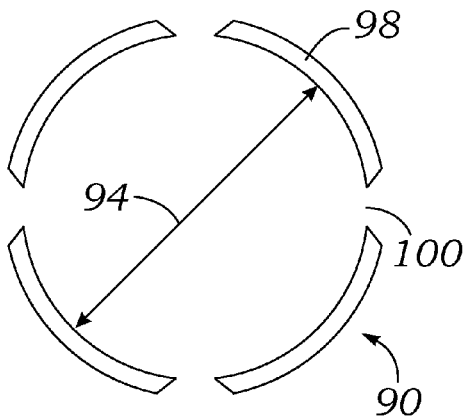

FIGS. 3A-3B depict an embodiment of a prosthetic heart valve support structure 90. The structure 90 comprises a substantially circular portion 92 defining an inner diameter 94. The substantially circular portion 92 comprises one or more thinned portions, such as notches 96, which in the particular embodiment are spaced about the circumference of the substantially circular portion 92, with thicker and stronger segments 98 of the substantially circular portion 92 extending between the notches 96. In the illustrated embodiment, there are four stronger segments 98 separated by four of the notches 96, although the number of segments may be more or less. The notches 96 or other thinned areas are configured to fail when subjected to the levels of radial expansive forces expected from a balloon catheter, such as 2, 3, 4, 5, or 6 atm. FIG. 3A depicts the structure 90 in its pre-dilation form. FIG. 3B depicts the structure 90 in its post-dilation form, where one or more of the notches 96 have broken so that there are one or more breaks 100 forming spaces between adjacent segments 98 of the substantially circular portion 92. The inner diameter 94 is larger in FIG. 3B to accommodate an expandable valve therein.

Figure 4A:
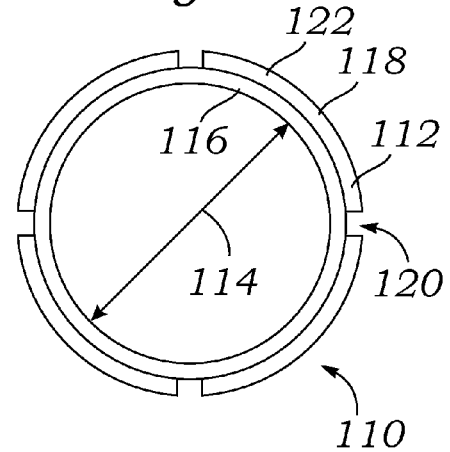
FIGS. 4A-4B depict top views in unexpanded and expanded configurations, respectively, of a prosthetic heart valve support structure according to an embodiment of the invention.
Figure 4B:
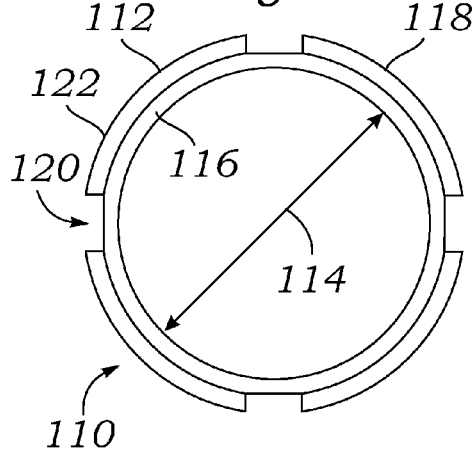

FIGS. 4A-4B depict a further embodiment of a prosthetic heart valve support 110, having a substantially circular portion 112 defining an inner diameter 114. The substantially circular portion 112 is a composite structure formed from two rings 116, 118 of similar and/or dissimilar materials. A first of the rings 116, which in the particular embodiment is an inner portion of the structure defining the inner diameter 114, is a substantially continuous ring structure. The second of the rings 118 is a segmented structure having breaks 120 (and/or weakened portions) between adjacent segments 122. It should be noted that in the illustrated embodiment there are four segments 122 comprising the outer ring 118, though more or less utilized. In an alternative embodiment, there are three outer segments 122 having breaks 120 distributed evenly around the circumference at 120° spacing. In a still further embodiment, the breaks 120 are located coincident with commissure posts of the heart valve support 110, such as posts 75 shown in FIGS. 2A-2D. The substantially circular portion 112 strongly resists compression, which inherently drives the adjacent segments 122 of the second portion 118 together so that both the first circular portion 116 and the second circular portion 118 resist such compression. The composite structure has much less resistance to radial expansion, which is resisted by the first circular portion 116 but is resisted not at all (or minimally) by the second circular portion 118. For example, the inner circular portion 116 may be made of an elastic material. Accordingly, the structure may radially expand when subjected to the levels of radial expansive forces expected from a balloon catheter, such as 2, 3, 4, 5, or 6 atm. As depicted in FIG. 4B, when the structure is radially expanded the breaks 120 between adjacent segments 122 grow larger, thereby increasing the inner diameter 114 of the structure in order to accommodate a new valve therein.

Figure 5A:
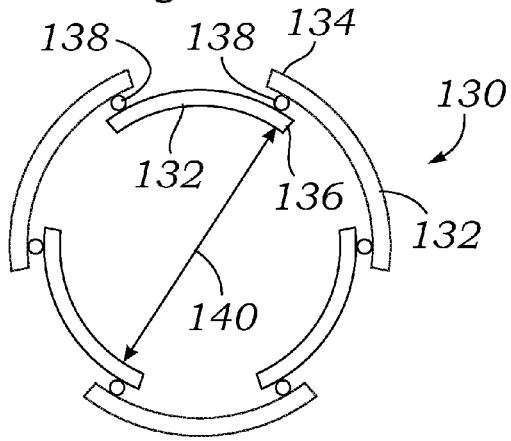
FIGS. 5A-5B depict top views of a prosthetic heart valve support structure in pre-dilation and post-dilation configurations, respectively, according to an embodiment of the invention.
Figure 5B:
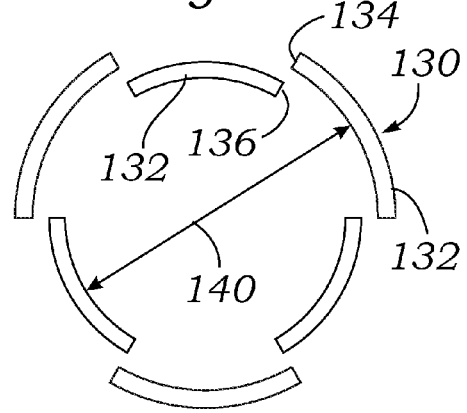

FIGS. 5A-5B depict a further embodiment of a prosthetic heart valve support structure 130 in pre-dilation and post-dilation configurations, respectively. The structure 130 is formed from multiple segments 132 with overlapping ends 134, 136 secured via connections 138. For example, the support structure 130 comprises a ring made of a plurality of inner segments 132 generally arranged on an inner circle and being spaced apart across gaps, and a plurality of outer segments 132 generally arranged on an outer circle, each outer segment spanning a gap between adjacent inner segments. In one embodiment, there are three inner segments and three outer segments. Desirably, the outer segments 122 are centered within valve cusps defined by the heart valve support structure 130, such as between commissure posts. The segments 132 can be formed from various materials, such as metals (e.g., stainless steel, cobalt-chromium (e.g., Elgiloy), nickel-titanium (e.g., Nitinol), etc.) or polymers such as polyester, etc. The connections 138 can be formed using spot welds, sonic welds, and/or adhesive. The connections are configured to fail when subjected to the levels of radial expansive forces expected from a balloon catheter, such as 2, 3, 4, 5, or 6 atm. When the connections 138 fail, the segments 132 slidingly move apart, reducing or eliminating the area of overlap of the ends 134, 136 and thereby increasing the size of the inner diameter 140.

Figure 6A:
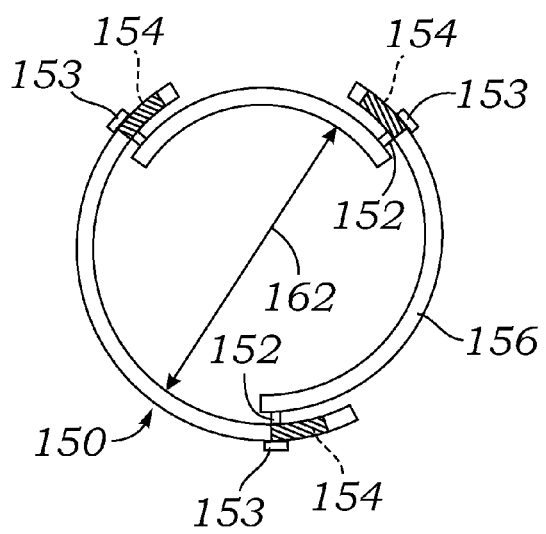
FIGS. 6A-6D depict top (pre-dilation), top (post-dilation), and close-up side views, respectively, of a prosthetic heart valve support structure according to an embodiment of the invention.
Figure 6B:
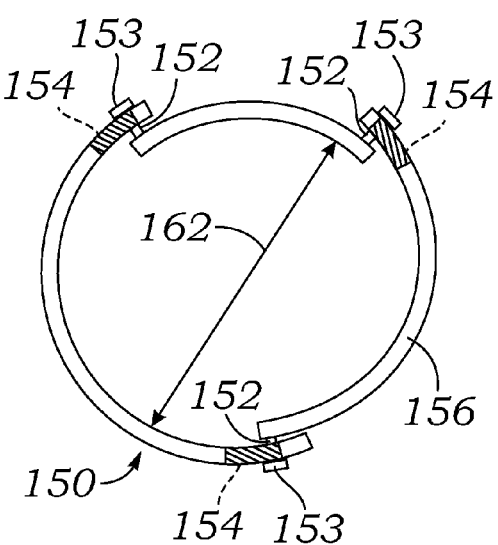
Figure 6C:
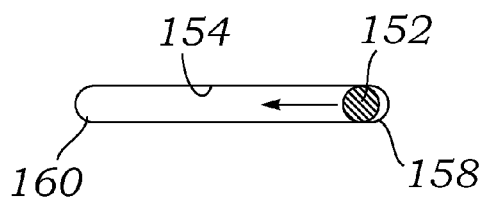
Figure 6D:
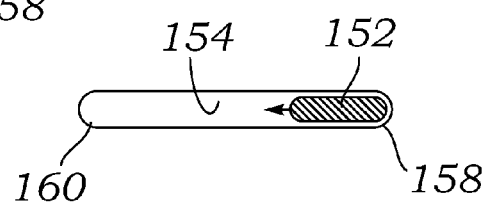

FIGS. 6A-6D depict a further embodiment of the invention, where a heart valve support structure 150 has a lock-out feature which prevents compression of the support structure and also prevents over-expansion of the support structure and hence of a prosthetic heart valve supported by the support structure 150. The support structure 150 has a plurality of expansion sections each comprising a pin 152 and slot 154 connecting adjacent segments 156. More specifically, a pin 152 of one segment 156 resides in a slot 154 of an adjacent segment 156, thereby slidingly connecting adjacent segments 156. The pin 152 may have an enlarged distal portion 153 having a diameter larger than the slot width, which thereby prevents the pin 152 from being pulled out of the slot 154. The pin 152 may have a substantially round cross section, as depicted in FIG. 6C, or a substantially elongated cross section, as depicted in FIG. 6D. Other cross sections, such as square or rectangular, are also within the scope of the invention. Note that the pin 152 and slot 154 may be configured so that the pin 152 resides very tightly within the slot 154, so that the pin 152 will not slide within the slot 154 unless subjected to a significant force, such as the force created when a balloon of a balloon catheter is expanded within the support 150 to a pressure of 2, 3, 4, 5, 6, 7, or 8 atmospheres or more. The pin 152 could be fixedly held at a specific position within the slot (e.g., at the proximal end 158 of the slot 154), such as via adhesive or spot-welding, but with the adhesive and/or spot-weld configured to fail and permit the pin 152 to slide when the structure 150 is subjected to a significant force, such as the force created when a balloon of a balloon catheter is expanded within the support 150 to a pressure of 2, 3, 4, 5, 6, 7, or 8 atmospheres or more. When the structure 150 is in its non-expanded (pre-dilation) condition, as depicted in FIG. 6A, the pin 152 is at the proximal end 158 of the slot 154 and the inner diameter 162 is at a minimum size. When the structure 150 is radially expanded (e.g., when the prosthetic valve that the structure 150 is supporting is dilated), as depicted in FIG. 6B, the pin 152 slides distally toward the distal end 160 of the slot 154 and the inner diameter 162 is enlarged. The pin 152 and slot 154 arrangement thus permits the structure 150 to radially expand, but provides a fixed limit on the maximum expansion that will be permitted. top (pre-dilation), top (post-dilation), and close-up side views, respectively, of a prosthetic heart valve support structure according to an embodiment of the invention;

FIGS. 7A-7D depict a further embodiment a support structure 170 according to the invention, where expansion sections are formed by a series of interconnected struts 172 connected end-to-end by hinge-like connections 174 to form a zig-zag accordion-like structure having substantially diamond-shaped cells 176. In the non-expanded (pre-dilation) configuration (depicted in FIGS. 7A and 7B), the substantially diamond-shaped cells 176 are at a maximum height 178 and a minimum width 180, and the structure 170 defines a minimum sized inner diameter 182. In the expanded (post-dilation) configuration (depicted in FIGS. 7C and 7D), the interconnected struts 172 have rotated at the hinge-like connections 174, and the substantially diamond-shaped cells 176 have thus been stretched sideways and are at a minimum height 178 and a maximum width 180. The expanded structure 170 defines a maximum sized inner diameter 182. The support structure 170 is desirably plastically-expandable so as to initially resist expansion after implant and when subjected to normal anatomical expansion pressures. When the time comes to implant a replacement valve within the prosthetic valve having the support structure 170, outward balloon or other mechanical-expander forces cause plastic deformation of the interconnected struts 172, typically at the hinge-like connections 174. The balloon or mechanical expansion forces can be done separately from implantation of a subsequent valve, or expansion of the subsequently-implanted valve can simultaneously expand the support structure 170.

FIGS. 8A-8B depict a further embodiment of a support structure 190 according to the invention, where expansion sections 191 extend between commissural supports 193. The expansion sections 191 are formed by a generally zig-zag or sinusoidal structure 192 formed by a series of segments 194 secured at peaks 196 in a serpentine pattern. In the non-expanded (pre-dilation) configuration of FIG. 8A, the zig-zag segments 194 are compressed closely together, with minimal distances 198 between adjacent peaks 196 (and may even have adjacent segments 194 contacting each other edge-to-edge and thus preventing inward compression of the structure to a smaller diameter). In such a configuration, the support structure 190 will have a minimal (unexpanded) diameter. In the expanded (post-dilation) configuration of FIG. 8B, the sinusoidal/zig-zags are pulled into a less compressed configuration, with the adjacent peaks 196 and segments 194 spaced apart from each other, with maximum distances 198 between adjacent peaks 196 and according a maximum diameter for the support structure 190.

Figure 9A:
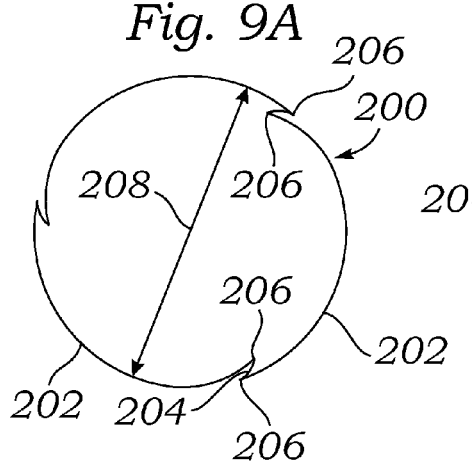
FIGS. 9A-9B depict top views, pre-dilation and post-dilation, respectively, of a prosthetic heart valve support structure according to an embodiment of the invention.
Figure 9B:
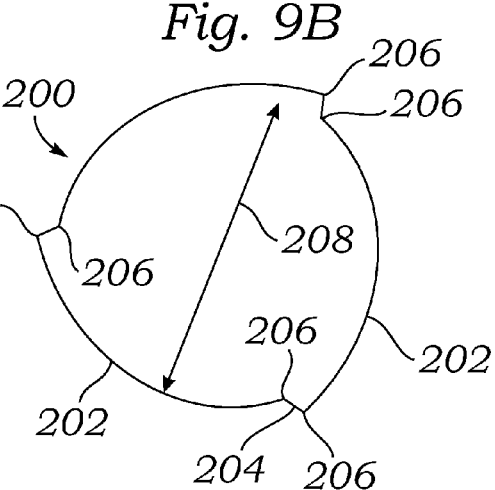

FIGS. 9A-9B depict a further embodiment of the invention, where a support structure 200 comprises segments 202 connected via hinge-like folds 204. In the non-expanded (pre-dilation) configuration of FIG. 9A, the ends 206 of adjacent segments 202 overlap at the folds 204, and the structure 200 has a minimum diameter 208. When the structure 200 is expanded (post-dilation) as depicted in FIG. 9B, the ends 206 of adjacent segments are pulled apart as the folds 204 at least partially unfold, so that the structure has a maximum inner diameter 208. Again, the folds 204 of the support structure 200 may be formed of a plastically-expandable material so that once expanded they retain their shape.

In embodiments of the invention, such as that depicted in FIGS. 7A-9B, the geometry and materials of the structure may be configured so that certain loads (e.g., compressive and/or expansive pressures up to 1 or 2 or even 3 atmospheres) will keep the material in its elastic region, so that it may expand and/or compress slightly when subjected to relatively small compressive and/or expansive loads but will return to its original shape once such loads are removed. The geometry and materials of the structure may be configured so that after a certain load is reached (such as 2, 3, 4, 5, or 6 atmospheres), plastic deformation will occur with permanent radial expansion. With such plastic deformation, individual elements may "lock out" and thus prevent further radial dilation of the structure.

Figure 10A:
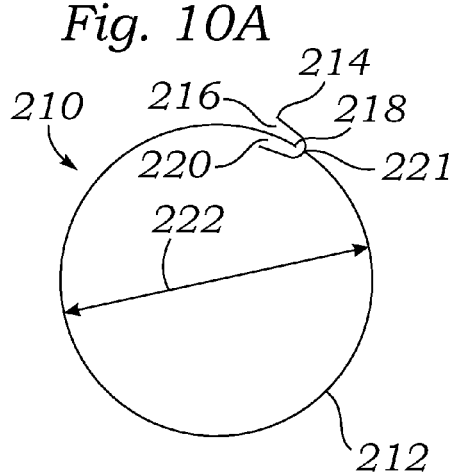
FIGS. 10A and 10B depict top views, pre-dilation and post-dilation, respectively, of a prosthetic heart valve support structure according to an embodiment of the invention.
Figure 10B:
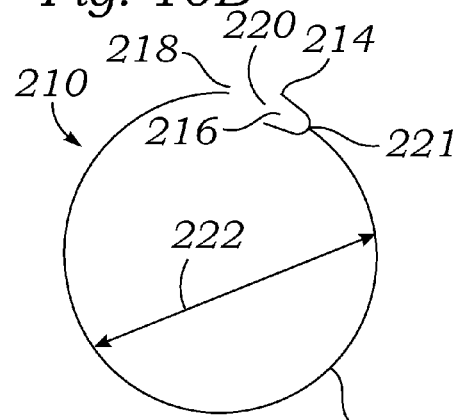

FIGS. 10A-10D depict a further embodiment of the invention, where a support structure 210 includes an arcuate segment 212, which in the particular embodiment is a segment of about 360 degrees passing around the entire circumference of the structure 210. A first end 214 of the arcuate segment 212 has a recess 216 configured to slidingly receive a second end 218 of the arcuate segment 214. The recess 216 has a distal opening 220 and a proximal end 221, with the second end 218 configured to be advanced into the recess 216 and to rest against the proximal end 221 thereof when the structure 210 is in its unexpanded (pre-dilation) configuration as depicted in FIG. 10A. The seating of the second end 218 against the proximal end 221 thus prevents the structure 210 from collapsing inwardly to an inner diameter 222 that is smaller than desired for the unexpanded (pre-dilation) configuration. When the structure 210 is radially expanded, as depicted in FIG. 10B, the second end 218 slidingly and distally moves out of the recess 216 until the second end is completely outside of the recess 216 and there is space between the first end 214 and the second end 218, with the structure having a larger inner diameter 222 than when in the unexpanded configuration of FIG. 10A. Note that while FIGS. 10A-10B depict a single arcuate segment 212 defining the entire circumference of the support structure 210, a plurality of arcuate segments, such as 2 segments of about 180 degrees each or 3 segments of about 120 degrees each, etc., could alternatively be used to form the circumference of the structure 210, with adjacent ends of adjacent segments having recesses and/or ends configured to interact as depicted in FIGS. 10A-10B (and/or FIGS. 10C-10F below).

Figure 10C:
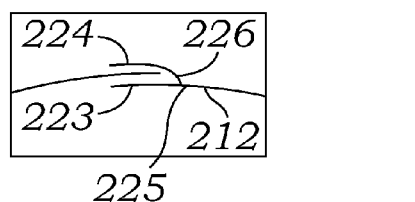
FIGS. 10C-10D depict top (close-up) views, pre-dilation and post-dilation, respectively, of a prosthetic heart valve support structure according to an embodiment of the invention.
Figure 10D:
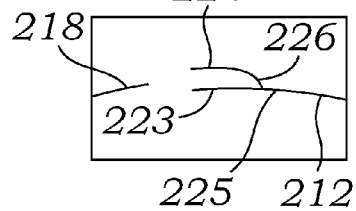

FIGS. 10C and 10D depict a modified version of the embodiment of FIGS. 10A-10B, where the recess 216 is configured so that the radially inward portion 223 thereof is substantially in circumferential alignment with the rest of the arcuate segment 212, while the radially outward portion 224 of the recess 216 extends radially outward from the arcuate segment 212. In this embodiment, the interior surface 225 of the structure (e.g., within the inner diameter) is relatively smooth, whereas the surface disruption created by the recess 216 assembly is almost entirely on the exterior surface 226 of the support structure 200. Such an assembly provides a smooth interior surface for the support structure 210, with a correspondingly consistent inner diameter.

Figure 10E:
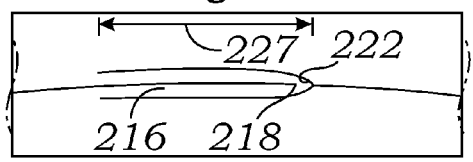
FIGS. 10E-10F depict top (close-up) views, pre-dilation and post-dilation, respectively, of a prosthetic heart valve support structure according to an embodiment of the invention.
Figure 10F:
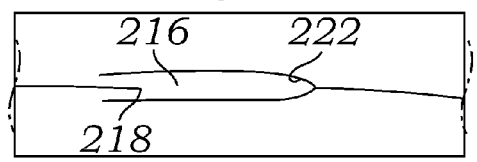

FIGS. 10E and 10F depicted another modified version of the embodiment of FIGS. 10A and 10B, where the recess 216 is relatively deep, having a depth 227 larger than in FIGS. 10A-10B, providing longer overlap between the recess 216 and the second end 218 which can provide more compression resistance and other increased structural integrity of the structure. The depth 227 of the recess may be sufficient to contain the second end 218 even after the second end 218 is distally displaced away from the recess proximal end 221 during expansion. Accordingly, the second end 218 always remains within the recess 216, even after expansion/dilation of the support structure 210 to its larger inner diameter. As depicted in FIG. 10A, in the unexpanded configuration the second end 218 is positioned adjacent and/or against the recess proximal end 221. When the structure is radially expanded as depicted in FIG. 10F, the second end 218 is moved distally with respect to the recess proximal end 221 but still remains within the recess 216.

Note that there are many variations of the above-cited embodiments, including various combinations of the various embodiments, all of which are in the scope of the invention. Segments of one embodiment can be combined with the expandable portions of other embodiments. Also, a particular support structure could have any combination of the above-discussed expandable portions.

FIGS. 11A-11D are perspective and exploded views of an exemplary prosthetic heart valve 228 of the prior art oriented around a flow axis 229. The heart valve 228 comprises a plurality (typically three) of flexible leaflets 230 supported partly by an undulating wireform 231 as well as by a structural stent 232. The wireform 231 may be formed from a suitably elastic metal, such as a Co—Cr—Ni alloy like Elgiloy, while the structural stent 232 may be metallic, plastic, or a combination of the two. As seen in FIG. 11B, outer tabs 233 of adjacent leaflets 230 wrap around a portion of the structural stent 232 at so-called commissures of the valve that project in an outflow direction along the flow axis 229. A soft sealing or sewing ring 234 circumscribes an inflow end of the prosthetic heart valve 228 and is typically used to secure the valve to a native annulus such as with sutures. The wireform 231 and structural stent 232 are visible in the figures, but are normally covered with a polyester fabric to facilitate assembly and reduce direct blood exposure after implant.

FIGS. 11C and 11D show the inner structural stent 232 in both assembled and exploded views. Although the general characteristics of the prosthetic heart valve 228 as seen in FIGS. 11A and 11B may be utilized in a number of different prosthetic heart valves, the illustrated structural stent 232 is that used in a particular heart valve; namely, pericardial heart valves manufactured by Edwards Lifesciences of Irvine, Calif. For example, the Perimount™ line of heart valves that utilize pericardial leaflets 230 features an inner stent 232 much like that shown in FIGS. 11C and 11D. In particular, the stent 232 comprises an assembly of two concentric bands—an outer band 235 surrounding an inner band 236. The bands 235, 236 are relatively thin in a radial dimension as compared to an axial dimension, and both have coincident lower edges that undulate axially up and down around the circumference. The outer band 235 exhibits three truncated peaks between three downwardly curved valleys, while the inner band 236 has generally the same shape but also extends upward at commissure posts 237. The downwardly curved valleys are typically termed cusps 238, as seen in FIG. 11C.

In the exemplary Perimount™ valves, the outer band 235 is metallic and is formed from an elongated strip of metal bent to the generally circular shape and welded as at 250. In contrast, the inner band 236 is formed of a biocompatible polymer such as Delrin which may be molded, and also may be formed as a strip and bent circular and welded (not shown). Both the outer and inner bands 235, 236 feature a series of through holes that register with each other so that the assembly can be sewn together, as schematically illustrated in FIG. 11C. The wireform 231 and the commissure posts 237 of the inner band 236 provide flexibility to the commissures of the valve which helps reduce stress on the bioprosthetic material of the leaflets 230. However, the inflow end or base of the valve 228 surrounded by the sewing ring 234 comprises the relatively rigid circular portions of the structural stent 232. The combination of the metallic outer and plastic inner bands 235, 236 presents a relatively dimensionally stable circumferential base to the valve, which is beneficial for conventional use. However, the same characteristics of the structural stent 232 that provide good stability for the surgical valve resist post-implant expansion of the valve. Consequently, the present application contemplates a variety of modifications to the structural stent 232 to facilitate expansion thereof.

FIGS. 12-14 are perspective, assembled and exploded views of a number of different embodiments of replacement structural bands for the prior art prosthetic surgical heart valve 228 shown in FIG. 11A that enables the heart valve to expand post-implementation.

Figure 12A:
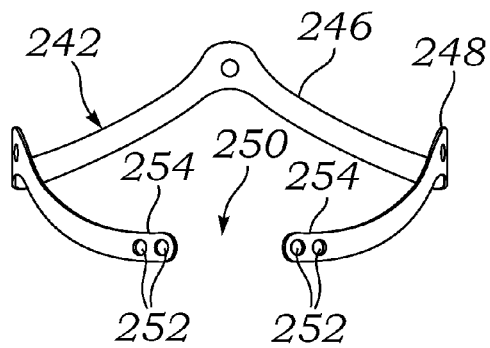
FIG. 12A depicts a side view of a prosthetic heart valve support band according to an embodiment of the invention.
Figure 12B:
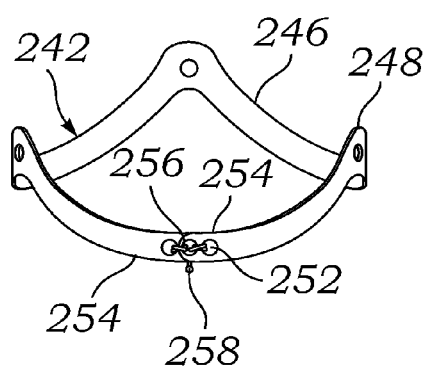
FIGS. 12B and 12C depict side and perspective (close-up) views, respectively, of the prosthetic heart valve support band of FIG. 12A with suture(s) securing the free ends together.
Figure 12C:
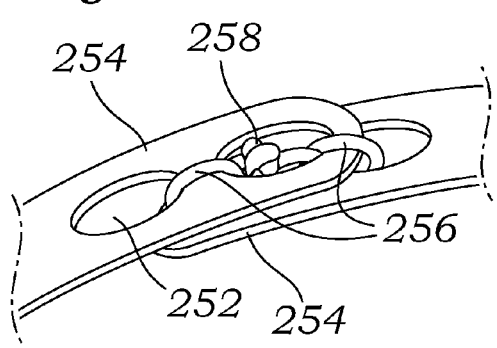
Figure 12D:
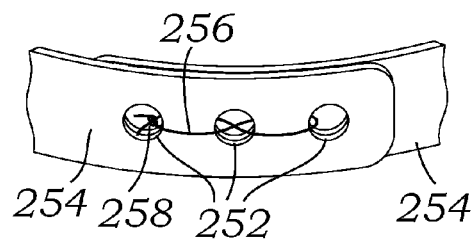
FIG. 12D shows an enlarged side view of the support band of FIG. 12A with an alternative configuration of free ends secured together.

In a first embodiment, FIGS. 12A-12F depict a composite support stent 240 for a prosthetic heart valve formed from an inner or first band 242 and an outer or second band 244. With reference to FIGS. 12A-12B, the first band 242 comprises a single, unitary piece of material forming a substantially circular support structure having 3 curved segments 246 connected at commissural points 248. One of the curved segments 246 has a break 250 in the middle thereof with holes 252 drilled in the free ends 254 on either side of the break 250. As shown in FIGS. 12B and 12C, when assembled the free ends 254 are joined together via a suture 256, such as silk 4-0 suture, passed through the holes 252 and secured in a knot 258. Note that the knot 258 may be formed on the radial exterior of the first support structure to help maintain a smooth interior surface thereof. FIG. 12D shows an enlarged side view of the outer support band 242 of FIG. 12A with an alternative configuration of free ends 254 secured together. In particular, each free end 254 has a series of holes 252, three as illustrated, that align with the same number of holes in the other free end. A length of suture 256 or other such filament may be interlaced through the holes 252 such as in a "FIG. 8" configuration, and then tied off at knot 258.

The suture/hole combination forms a weakened spot on the first band 242, where the suture 256 will break before the remaining parts of the support portion will fail when the support portion is subjected to a dilation force. Note that other techniques and assemblies may be used to form the weakened portions, such as spot welds, thinned sections, and other methods such as those disclosed herein for other embodiments. In this particular embodiment depicted in FIGS. 12A-12B, the first band 242 is desirably formed from a metal such as stainless steel or cobalt-chromium (Co—Cr).

Figure 12E:
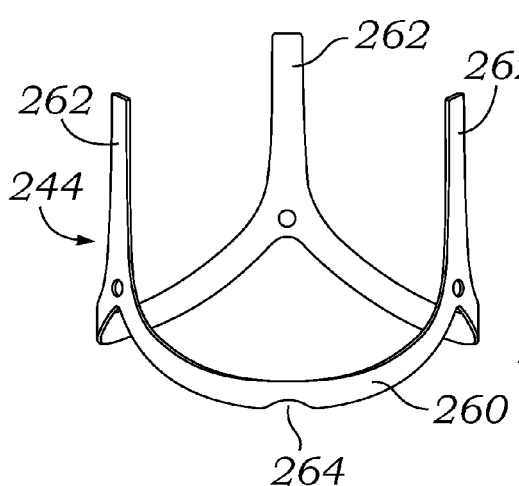
FIG. 12E depicts a side view of another prosthetic heart valve support band for use with the support band of FIG. 12A.

FIG. 12E depicts a second support band 244 according to an embodiment of the invention. The support band 244 comprises a single, unitary piece of a material, such as a polymer like polyester, forming a substantially circular support structure having 3 curved segments 260 connected at commissural supports 262. One of the curved segments 260 has a thinned section 264 to form a weakened section that will fail prior to the rest of the structure when subjected to a sufficient dilatation force. Note that other methods of forming the weakened section are also within the scope of the invention, such as using spot welds, sonic welds, sutures, and/or thinned/weakened areas.

Figure 12F:
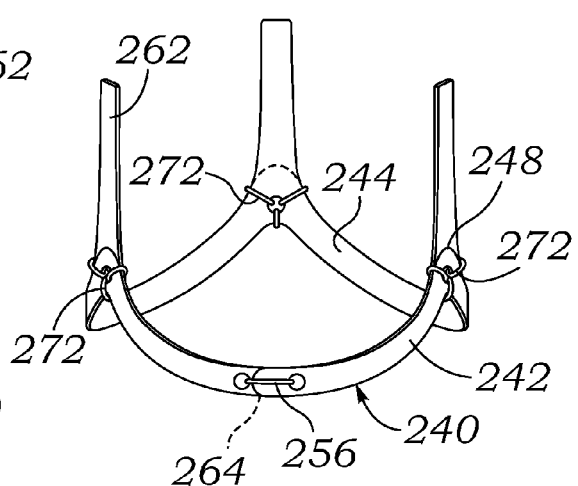
FIG. 12F depicts a side view of a prosthetic heart valve structure formed from securing the first prosthetic heart valve support band in FIG. 12A and the second prosthetic heart valve support band in FIG. 12E into a composite structure.
Figure 12H:
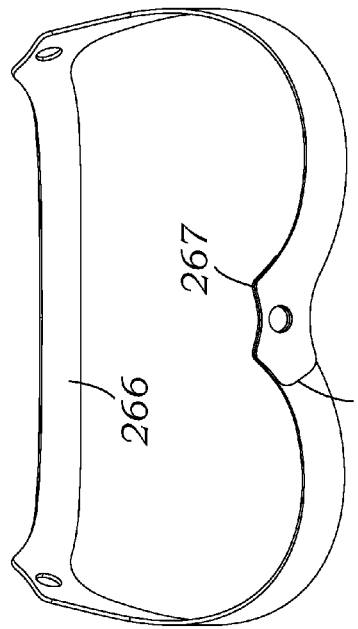
FIGS. 12G-12J show a variation on the first and second prosthetic heart valve support bands shown in FIGS. 12A-12F.

FIG. 12F depicts a composite prosthetic heart valve support stent 240 formed from securing the first prosthetic heart valve support band 242 and the second prosthetic heart valve support band 244 into a composite structure. The support portions 242, 244 may be secured together via various techniques, such as welds, adhesives, etc. In the particular embodiment depicted, the support portions 242, 244 are secured together via sutures 272 adjacent the commissural points 248 and commissural supports 262 of the support portions 242, 244. Note that in this particular embodiment, the first support band 242 is positioned concentrically within the second support band 244, and the weakened area 264 of the second band 244 is positioned adjacent the suture 256 over the overlapping ends 254 in the first band 242, so that when the second support band 244 and the first support band 242 break due to dilation the respective breaks will be at the same position around the circumference of the support stent 240.

In an alternate embodiment, the weakened area 264 might be circumferentially displaced from the suture 256 and overlapping ends 254, such as being position anywhere from a few degrees to being completely opposite (i.e., 180 degrees) away around the circumference. The weakened area 264 of the second support band 244 may be circumferentially displaced from the suture 256/overlapping ends 254, but still positioned between the same pair of commissure posts 262 between which the suture 256 overlapping ends 254 are positioned. Note that one or both of the first and second support bands 242, 244 may have multiple weakened areas designed to fail when subjected to sufficient radial pressure. For example, the first support band 242 may have a single weakened area in the form of the suture 256 and overlapping ends 254, with the second support band 244 having multiple weakened areas 264 (such as 3 different weakened areas, with one weakened area being positioned between each pair of commissural posts 262). The offsetting of the weakened areas of the first and second support portions may improve the structural integrity of the structure post-dilation.

Figure 12J:
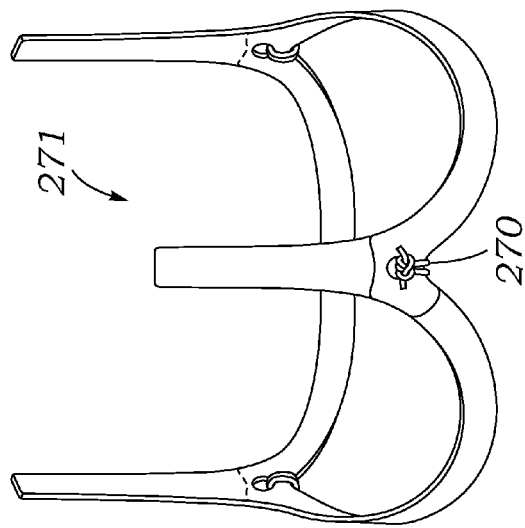
Figure 12G:
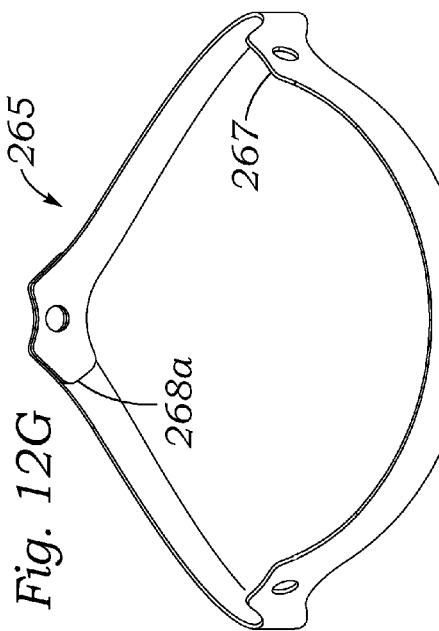
Figure 12I:
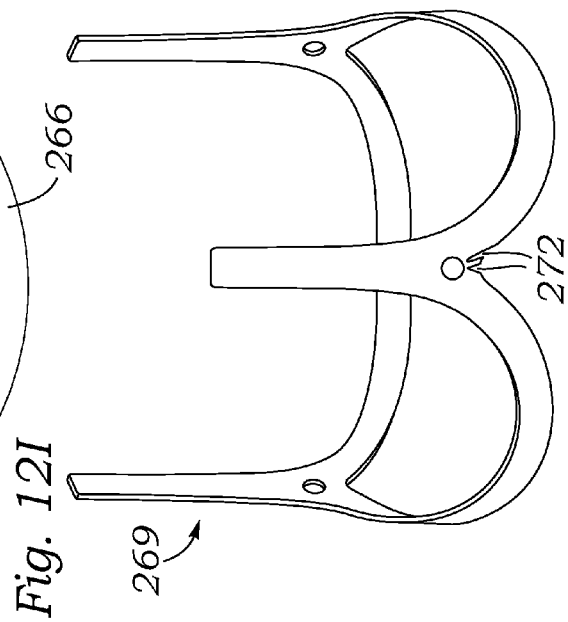
Figure 13A:
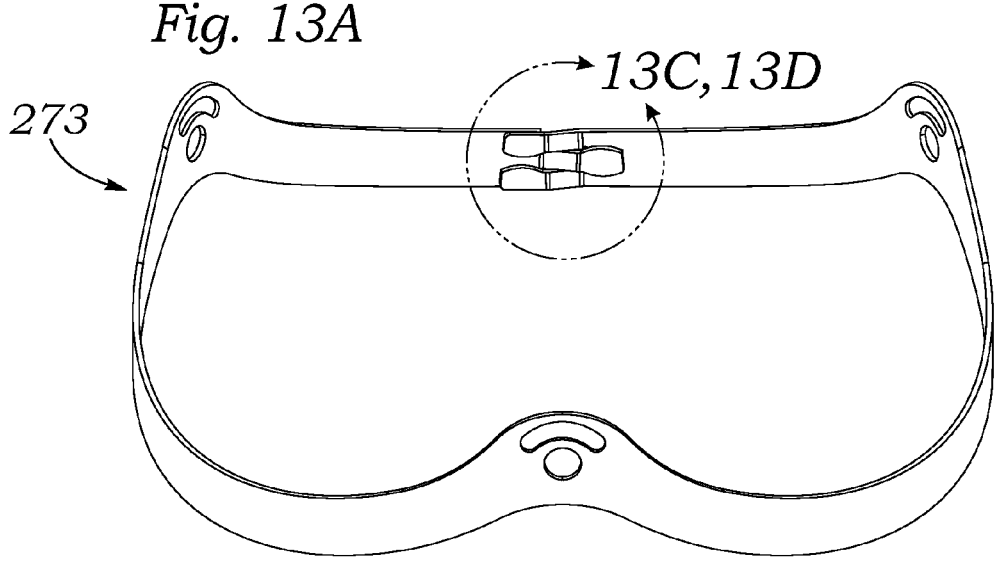
FIGS. 13A and 13B are perspective views of another exemplary prosthetic heart valve support band adapted for post-implant expansion having overlapping free ends with tabs that engage each other.
Figure 13B:
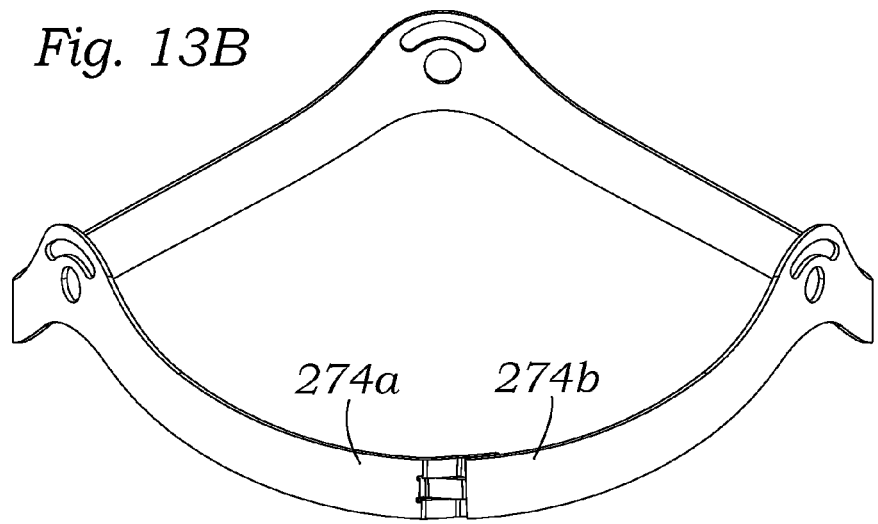
Figure 13C:
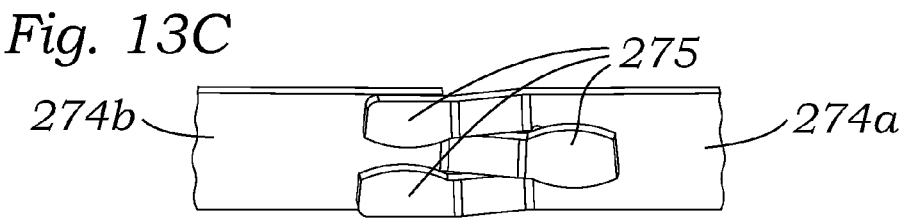
FIGS. 13C and 13D are enlarged views of the overlapping free ends in both constricted and expanded configurations, respectively.
Figure 13D:
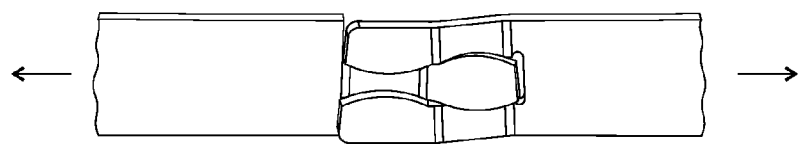

FIGS. 12G-12J show a variation on the first and second prosthetic heart valve support bands shown in FIGS. 12A-12F in which an outer or first band 265 includes the aforementioned undulating cusps 266 and truncated commissures 267, and is formed from a single element having two free ends 268a, 268b adjacent one of the commissures rather than at a cusp. When registered with an inner or second band 269, sutures 270 may be used to secure the registered commissure regions together such as by using aligned holes to form a composite stent 271, as seen in FIG. 12J. After assembly into a prosthetic heart valve, such as the valve 130 of FIG. 5A, the stent 271 initially provides good circumferential support for the valve and resists both compression or expansion from natural cardiac cycling forces. At some future date, if the valve requires replacement, a balloon or other mechanical expander may be advanced to the annulus and inserted into the orifice defined within the valve. The sutures 270 at the valve commissure having the free ends 268a, 268b will ultimately break from the outward expansion force of the balloon, permitting the valve to expand. Preferably the inner band 269 is made of a polymer that possesses relatively little resistance to the balloon forces, and eventually will stretch and even rupture. To facilitate this process, one or more small notches 272 such as seen in FIG. 12I may be provided at the bottom edge of the commissure of the inner band 269. Locating the break point at one of the commissures has an added benefit of allowing the valve to expand without changing much the circumferential spacing of the commissure posts. That is, in valves having three posts (and three leaflets) spaced apart 120°, for example, the lower cusps 266 of the outer band 265 will slide apart slightly, as will the cusp portions of the inner band 269, but the upstanding posts will remain essentially in the same position. The expansion magnitude is not so great as to distort the structure, and so the upstanding posts of the primary valve will remain 120° apart so as not to interfere with the functioning of a secondary valve or affect the ability of the valve sinuses (in aortic valves) to move and facilitate flow.

FIGS. 12K-12M show further variations on the first prosthetic heart valve support band 265. A modified outer band 265' in FIG. 12K includes two free ends at one of the cusps 266' that remain aligned with several wrap-around tabs (not numbered). The tabs of one free end that initially extend axially relative to the band axis may be bent around the other free end during assembly. Notches or shoulders on one or the other prevents the band 265' from being compressed, but the arrangement permits expansion, such as with a dilation force within the valve. In testing, the overlapping tab configuration in FIG. 12K produced an average breaking pressure of about 3.17 atm, with a range of between 1 to 5 atm. FIG. 12L shows another modified outer band 265" with the free ends at a cusp 266" that overlap; one radially sliding inside the other. Instead of a flexible sleeve, as in FIGS. 13A-13B below, a suture is wrapped around multiple times, e.g., four, to maintain alignment of the two free ends. Furthermore, small tabs (not numbered) extend radially outward from each free end to present an impediment to compression of the band, but the tabs are positioned and angled such that they do not unduly interfere with expansion of the band 265". When tested for break strength, the configuration in FIG. 12L produced an average breaking pressure of about 3.0 atm, with a range of between 2 to 4.25 atm. FIG. 12M illustrates a still further alternative band 265'" having overlapping free ends at a cusp 266'". A small tab on the inner free end passes outward through a similar-sized slot in the outer free end, something like a belt buckle. The tab may be shaped like an arrowhead to provide a lock of sorts and prevent its removal from the slot. Again, this limits relative movement of the two free ends to one direction that enables expansion of the band but prevents compression. The break strength for the belt buckle structure in FIG. 12M is between about 6.5 to 8 atm.

Finally, FIG. 12N shows a commissure portion of a still further outer band 265"" that has a polymer rivet with male part A and female flange B secured through the aligned holes. The rivet A/B may be snap fit together or fused through heating or ultrasonic welding. A variation is a polymer pin or screw that passes through the aligned holes and engages both free ends of the band by swaging the ends, adhesive or with threads. The force needed to separate the ends and expand the band 265"" depends on the type of polymer used. One other alternative is to form the rivet A/B of a biodegradable material that will maintain the band together for a period after implant and then dissolve, enabling easy expansion of the band 265"". Still further, material from one of the holes may be mechanically deformed into the other hole, such as by swaging, to provide some interference which can be overcome when needed by a dilatory force. Of course, combinations of these structures are also possible, such as combining the belt-buckle tab/slot with the wrap-around tabs.

Now with reference to FIGS. 13A-13D, a still further alternative first or outer band 273 is shown that may be used with any of the various expandable heart valves disclosed herein. The band 273 has two free ends 274a, 274b that overlap in the area of one of the cusps of the band. The free ends 274a, 274b include interlaced tabs 275 that permit the two ends to slide away from one another. In the illustrated embodiment, one free end 274a has a pair of tabs 275 that surround a single tab on the other free end 274b. The tabs desirably each include an enlarged head portion and slimmer stem, with the head portions overlapping radially and engaging at a particular outward expansion. The free ends 274a, 274b thus prevent contraction of the band 273 and permit a limited expansion thereof. The expansion requires a relatively low force to cause the free ends 274a, 274b to slide with respect to one another, and the band 273 is desirably coupled with an inner band with a weakened cusps, such as shown at 244 in FIG. 11E. The same interlaced structure may be provided at all three cusps, or at the commissures, though the cusp regions are well suited for the structure.

Figure 14A:
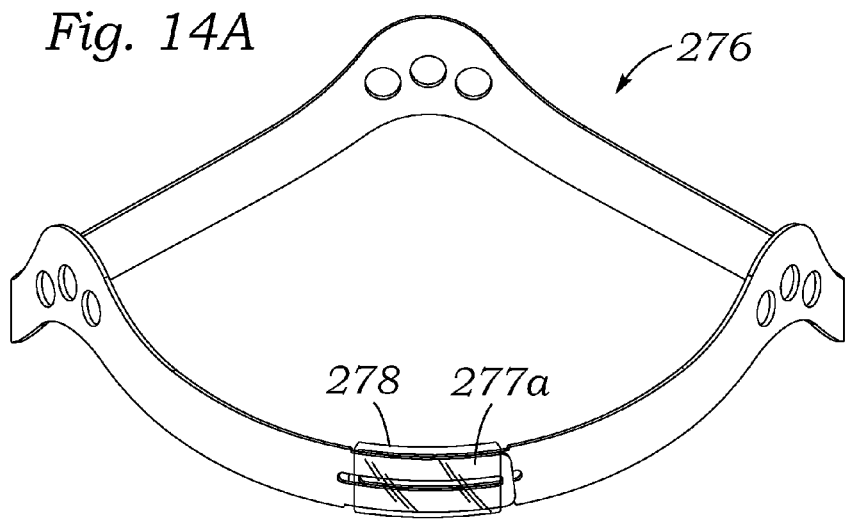
FIGS. 14A and 14B are perspective views of a further prosthetic heart valve support band adapted for post-implant expansion also having overlapping free ends held together by a frictional sleeve.
Figure 14B:
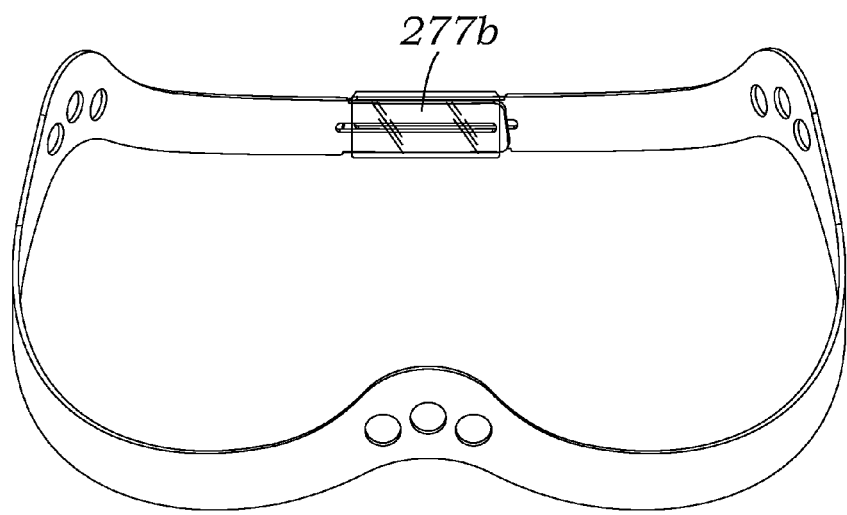
Figure 14C:
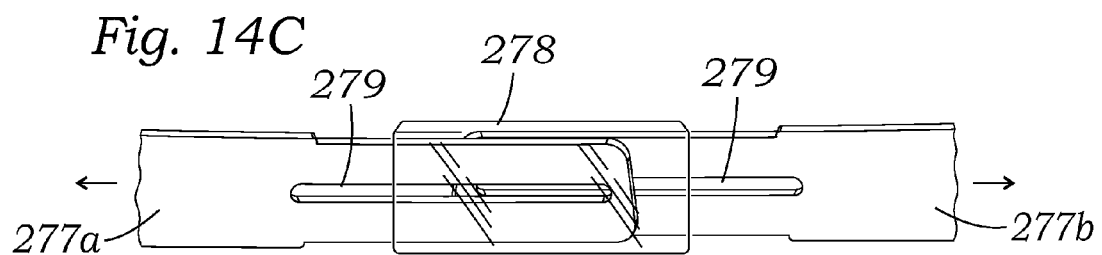
FIG. 14C shows the expansion of the overlapping free ends.

Finally, FIGS. 14A-14 show another "sliding" engagement wherein a first or outer band 276 includes two overlapping free ends 277a, 277b that slide with respect to one another. The free ends 277a, 277b are substantially rectangular in shape and one resides radially within and against the other. A sleeve 278 surrounds the free ends 277a, 277b and holds them radially together. The sleeve 278 desirably comprises an elastic material, such as silicone rubber, and is shown transparent to illustrate the mating free ends 277a, 277b. With reference to the enlargement in FIG. 14C, the two free ends 277a, 277b may slide apart a predetermined distance while still being overlapping. The flexible sleeve 278 provides a minimum amount of friction but generally just serves to maintain alignment of the free ends 277a, 277b. Each of the free ends 277a, 277b further includes a circumferentially-oriented slot 279 that stops short of the terminal ends and provides a pathway for fluid flow. As seen in FIGS. 14A and 14B, the slots 279 extend farther outward from the sleeve 278 so that fluid can always enter the spaced within the sleeve. During assembly and storage, the slots 279 permit flow of a fluid between the overlapping free ends 277a, 277b to allow for sterilization.

FIG. 15A depicts an expandable prosthetic heart valve deployment catheter 320 configured for (prior) prosthetic heart valve dilation and (replacement) expandable prosthetic heart valve deployment. The deployment catheter 320 has an elongated main body 322, a proximal end 324, and a distal end 326. The proximal end 324 includes a handle 328. The distal end 326 includes a dilation balloon 330 upon which an expandable prosthetic valve 332 is mounted. In the particular embodiment depicted, the expandable prosthetic valve 332 includes a stent 334. The distal end 326 may also include one or more radiopaque markers 333 or similar visibility markers to improve visibility of the device within the patient when using fluoroscopy or other viewing technologies.

FIGS. 15B-15D depict deployment of an expandable prosthetic heart valve 332 within a heart valve annulus 336 where a prosthetic heart valve 318 has previously been deployed. The previously-deployed prosthetic heart valve 318 may have been deployed using any methods, including methods currently known in the art such as traditional (open chest) surgery, minimally-invasive (e.g., keyhole) surgery, and percutaneous surgery. Depending on the particular application, the previously-deployed prosthetic heart valve 318 can be deployed in the patient years prior to, days prior to, hours prior to, or immediately prior to deployment of the expandable prosthetic heart valve 332 as depicted in FIGS. 15B-15D.

FIG. 15B depicts the expandable prosthetic heart valve deployment catheter 320 of FIG. 15A with the distal end 326 advanced so that the dilation balloon 330 and expandable prosthetic heart valve 332 are positioned within the previously-deployed prosthetic heart valve 318 in the patient's heart 340. The previously-deployed prosthetic heart valve 318 is seen in cross-section to show the generally rigid and/or expansion-resistant support frame 338.

In the particular embodiment depicted in FIG. 15B, the deployment catheter 320 has been advanced over a guide wire 342, which was advanced into the patient's heart 340 and previously-deployed prosthetic heart valve 318 prior to advancement of the deployment catheter 320 into the patient. Note that the use of a guide wire 342 is optional. Other guide devices could also be used, in addition to or in lieu of a guide wire. For example, a guide catheter could be used, wherein a guide catheter is advanced to a desired position within a patient, and the deployment catheter is then advanced into the patient inside of the guide catheter until the distal end of the deployment catheter extends from a distal opening in the guide catheter. A deployment catheter could also be used without any sort of guide wire or guide catheter, so that the deployment catheter is guided by itself into the desired treatment location.

As depicted in FIG. 15C, once the dilation balloon 330 and expandable prosthetic heart valve 332 are properly positioned within the heart valve annulus and previously-deployed prosthetic heart valve 318, the dilation balloon 330 is expanded. The expanding dilation balloon 330 forces the stent 334 to expand outwardly, and forces the leaflets of the previously-deployed prosthetic heart valve 318 against the heart valve annulus 336. The force from the expanding dilation balloon 330 also dilates the previously-deployed prosthetic heart valve 318, forcing the support frame 338 of the previously-deployed prosthetic heart valve 318 to expand.

In FIG. 15D, the dilation balloon 330 is deflated or otherwise reduced in diameter, with the new expandable prosthetic valve 332 deployed in the heart valve annulus 336 and previously-deployed prosthetic heart valve 318, and also held in place by the stent 334. The outward pressure from the expanded stent 332, along with the inward pressure from the heart valve annulus 336 and from any elastic portions (such as core, cords, and/or or covers) of the previously-deployed prosthetic heart valve 318 or from the previously-deployed prosthetic heart valve leaflets 344, combine to firmly seat the new expandable prosthetic valve 332 in the desired position in the heart valve annulus 336 and previously-deployed prosthetic heart valve 318. The deployment catheter 320 with the dilation balloon 330 can then be withdrawn from the heart 340, leaving the new expandable prosthetic heart valve 332 in its deployed position within the patient and the previously-deployed prosthetic heart valve 318.

In a further embodiment of the invention, the previously-deployed prosthetic heart valve 318 is dilated in a separate step from deployment of the expandable prosthetic heart valve 332. FIG. 16A depicts an expandable prosthetic heart valve deployment catheter 320 configured for previously-deployed prosthetic heart valve dilation and expandable prosthetic heart valve deployment using two separate balloons, and more specifically a distal balloon 330a and a proximal balloon 330b. The distal balloon 330a is configured to deploy the new expandable prosthetic valve 332, which is positioned on the distal balloon 330a, whereas the proximal balloon 330b is configured for dilation of the previously-deployed prosthetic heart valve 318.

FIGS. 16B-16D depict dilation of the previously-deployed prosthetic heart valve 318 and valve annulus 336 using the proximal balloon 330b. In FIG. 16B, the deployment catheter 320 has been advanced into the heart 330 with the distal balloon 330a (with expandable prosthetic valve 332 thereon) advanced past the previously-deployed prosthetic heart valve 318, and the proximal balloon 330b positioned within the previously-deployed prosthetic heart valve 318 and valve annulus 336.

The proximal balloon 330b is inflated or otherwise expanded, as depicted in FIG. 16C, thereby dilating the previously-deployed prosthetic heart valve 318 and valve annulus 336. The support frame 338 of the previously-deployed prosthetic heart valve 318 is expanded, similarly to the changes previously discussed with respect to the dilation discussed in connection with FIG. 16C above.

After dilation of the previously-deployed prosthetic heart valve 318, the proximal balloon 330b is deflated or otherwise reduced in diameter, as depicted in FIG. 16D. The deployment catheter 320 may then be withdrawn from the patient until the proximal balloon 330b is proximal of the previously-deployed prosthetic heart valve 318 and the distal balloon 330a is positioned within the previously-deployed prosthetic heart valve 318. The distal balloon 330a will be positioned within the previously-deployed prosthetic heart valve 318 in a similar fashion to that depicted for balloon 330 in FIG. 15B. The distal balloon 330a will then be expanded to deploy the expandable prosthetic valve 332 in essentially the same manner as was discussed and depicted in FIGS. 15B-15D. The distal balloon 330a will serve to deploy the new expandable prosthetic valve 332, and may also serve to further dilate the previously-deployed prosthetic heart valve 318 and/or native valve annulus 336.

Note that in an alternate embodiment two separate catheters are used for dilating the previously-implanted prosthetic valve. The first balloon catheter is a traditional dilation catheter and is advanced into the patient to a position within the previously-deployed heart valve. The balloon of the first balloon catheter is expanded to a desired pressure (e.g., 4-5 atm) sufficient to dilate (radially expand) the previously-implanted prosthetic valve. The first balloon catheter is then withdrawn from the patient, and a second balloon catheter (such as that depicted in FIGS. 15A-15D) with balloon and new expandable prosthetic heart valve thereon is advanced into the patient, the balloon is expanded to deploy the new expandable prosthetic heart valve within the previously-implanted (and now dilated) prosthetic heart valve, and the second balloon catheter is withdrawn from the patient.

Note that the expandable prosthetic valve may be self-expanding, in which case the deployment catheter may not have a dilation balloon as depicted in FIGS. 15A-15D and 16A-16D. Moreover, such a self-expanding prosthetic heart valve could be deployed with or without prior dilation of the previously-deployed prosthetic heart valve. For example, a self-expanding prosthetic heart valve may provide sufficient outward radial force to dilate the previously-deployed prosthetic heart valve and/or to hold a now-dilated previously-deployed prosthetic heart valve in an expanded configuration in order to provide sufficient room for the self-expanding prosthetic heart valve in its expanded configuration.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A prosthetic heart valve having an inflow end and an outflow end, the prosthetic heart valve having a first unexpanded configuration and a second expanded configuration, the prosthetic heart valve comprising:
    an inner support structure defined around a valve orifice, the support structure having a first inner diameter when the prosthetic heart valve is in the first unexpanded configuration and a second inner diameter when the prosthetic heart valve is in the second expanded configuration, the support structure configured when in the first unexpanded configuration to resist inward compression of the support structure and to permit radial expansion of the support structure to the second inner diameter when subjected to a dilation force, the support structure comprising a radially thin outer metallic support ring having an undulating shape with three downward cusps alternating with three upward truncated commissures around its circumference and including a single expansion segment that will plastically expand when subjected to the dilation force, the support structure further including a radially thin stent ring disposed in concentric abutment with and radially inside the support ring and being continuous and integrally formed of a polymeric material, the stent ring defining commissure posts aligned with and extending above the truncated commissures of the support ring and cusp portions aligned with the support ring cusps, wherein the support ring and the stent ring are secured together with a suture passing radially through both at a point around their common circumference, the stent ring having weakened areas below each of the commissure posts configured to break before other portions of the stent ring when the support ring expands; and
    a valve portion supported by the support structure that allows for one-way blood flow through the valve when the valve is in the first unexpanded configuration.

2. The prosthetic heart valve of claim 1, wherein the expansion segment comprises a series of interconnected struts connected end-to-end by hinge-like connections which forms an accordion-like structure having substantially diamond-shaped cells.

3. The prosthetic heart valve of claim 1, wherein the valve portion has flexible leaflets and further including a cloth covering surrounding the support structure and facilitating attachment of peripheral edges of the flexible leaflets along an outflow edge of the support structure.

4. The prosthetic heart valve of claim 1, wherein the expansion segment comprises a serpentine structure formed by metallic struts.

5. The prosthetic heart valve of claim 4, wherein the struts are compressed closely together, with minimal distances between adjacent struts in the unexpanded configuration to prevent inward compression of the structure to a smaller diameter.

6. A prosthetic heart valve having a first unexpanded configuration and a second expanded configuration, the prosthetic heart valve comprising:
    a support structure defining a circumference, the support structure having a first inner diameter when the prosthetic heart valve is in the first unexpanded configuration and a second inner diameter when the prosthetic heart valve is in the second expanded configuration, wherein the second inner diameter is larger than the first inner diameter, wherein the support structure resists inward compression when the prosthetic heart valve is in the first unexpanded configuration, the support structure comprising a support band with circumferentially overlapping free ends with at least one hole each that register and are circumferentially aligned and a weakened section comprising a suture passing radially through the registered hole(s) and is secured by tying that maintains the free ends aligned but is configured to structurally fail when the support structure is subjected to a dilation force greater than forces associated with normal cardiac cycling, the support structure further including a stent band connected to the support band and having upstanding commissure posts;
    a valve portion having flexible leaflets supported by the support structure that allows for one-way blood flow through the valve when the valve is in the first unexpanded configuration; and
    an undulating wireform covered with fabric to which the valve leaflets are partially connected around their peripheral edges, and the leaflets include outwardly-projecting tabs that pass outside of the wireform and attach to the commissure posts of the stent band.

7. The prosthetic heart valve of claim 6, wherein the support band has an undulating shape with alternating cusp and commissure portions, and the free ends overlap at one of the cusp portions.

8. The prosthetic heart valve of claim 6, wherein the support band has an undulating shape with alternating cusp and commissure portions, and the free ends overlap at one of the commissure portions.

9. The prosthetic heart valve of claim 6, wherein the stent band is arranged concentrically within the support band.

10. The prosthetic heart valve of claim 9, wherein the support band and the stent band are secured together at at least one point around the circumference of the support structure.

11. The prosthetic heart valve of claim 9, wherein the stent band comprises a polymeric material and the support band comprises a metal.

12. The prosthetic heart valve of claim 9, wherein the stent band comprises a weakened section configured to stretch or structurally fail when the support structure is subjected to the dilation force.

13. The prosthetic heart valve of claim 6, wherein the stent band commissure posts are aligned with and extend above the commissure portions of the support band and the stent band has cusps aligned with the support band cusp portions, and there are a plurality of weakened sections in the stent band located at each of the commissure posts.

14. The prosthetic heart valve of claim 6, wherein the support band comprises a metal and each overlapping free end has a series of holes that circumferentially align with the same number of holes in the other overlapping free end.

15. The prosthetic heart valve of claim 14, wherein the support band has an undulating shape with alternating cusp and commissure portions, and the free ends overlap at one of the cusp portions.

16. The prosthetic heart valve of claim 6, further including a cloth covering surrounding the support structure and facilitating attachment of peripheral edges of the flexible leaflets along an outflow edge of the support structure.

17. The prosthetic heart valve of claim 12, wherein the stent band includes a plurality of structurally weakened areas at an inflow edge below each of the commissure posts.

18. The prosthetic heart valve of claim 17, wherein the structurally weakened areas comprise notches at the inflow edge of the stent band.

19. The prosthetic heart valve of claim 6, further including a unique identifier on the support structure visible from outside the body after implant that identifies the support structure as being expandable.

20. The prosthetic heart valve of claim 1, further including a unique identifier on the support structure visible from outside the body after implant that identifies the support structure as being expandable.

* * * * *